(12) United States Patent
Conkling et al.

(10) Patent No.: US 6,911,541 B2
(45) Date of Patent: Jun. 28, 2005

(54) **PROMOTER FRAGMENT THAT IS RECOGNIZED BY THE PRODUCT OF THE TOBACCO *NIC* GENE**

(75) Inventors: Mark A. Conkling, Chapel Hill, NC (US); Yan Li, Durham, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/941,042

(22) Filed: Aug. 28, 2001

(65) Prior Publication Data

US 2003/0018997 A1 Jan. 23, 2003

Related U.S. Application Data

(60) Provisional application No. 60/229,198, filed on Aug. 30, 2000.

(51) Int. Cl.[7] .............................................. C12N 15/11
(52) U.S. Cl. ..................................................... 536/24.1
(58) Field of Search ........................ 536/24.1; 800/278, 800/317.3, 287, 298; 435/419, 469, 470, 320.1

(56) References Cited

U.S. PATENT DOCUMENTS

| | | |
|---|---|---|
| 4,693,976 A | 9/1987 | Schilperoort et al. |
| 4,762,785 A | 8/1988 | Comai |
| 4,885,248 A | 12/1989 | Ahlquist |
| 4,940,838 A | 7/1990 | Schilperoort et al. |
| 4,945,050 A | 7/1990 | Sanford et al. ............. 435/172 |
| 4,954,442 A | 9/1990 | Gelvin et al. |
| 5,034,322 A | 7/1991 | Rogers et al. |
| 5,036,006 A | 7/1991 | Sanford et al. |
| 5,100,792 A | 3/1992 | Sanford et al. |
| 5,107,065 A | 4/1992 | Shewmaker et al. |
| 5,149,645 A | 9/1992 | Hoekema et al. |
| 5,157,115 A | 10/1992 | Taniguchi ................... 536/227 |
| 5,179,022 A | 1/1993 | Sanford et al. ............. 435/287 |
| 5,190,931 A | 3/1993 | Inouye et al. |
| 5,204,253 A | 4/1993 | Sanford et al. .......... 435/172.3 |
| 5,208,149 A | 5/1993 | Inouye et al. |
| 5,231,020 A | 7/1993 | Jorgensen et al. ....... 435/172.3 |
| 5,254,800 A | 10/1993 | Bird et al. |
| 5,260,205 A | 11/1993 | Nakatani et al. ............ 435/193 |
| 5,272,065 A | 12/1993 | Inouye et al. |
| 5,283,184 A | 2/1994 | Jorgensen et al. ....... 435/172.3 |
| 5,352,605 A | 10/1994 | Fraley et al. |
| 5,356,799 A | 10/1994 | Fabijanski et al. |
| 5,365,015 A | 11/1994 | Grierson et al. |
| 5,369,023 A | 11/1994 | Nakatani et al. ............ 435/193 |
| 5,371,015 A | 12/1994 | Sanford et al. ............. 435/287 |
| 5,451,514 A | 9/1995 | Boudet et al. |
| 5,453,566 A | 9/1995 | Shewmaker et al. |
| 5,459,252 A | 10/1995 | Conkling et al. |
| 5,464,763 A | 11/1995 | Schilperoort et al. |
| 5,478,744 A | 12/1995 | Sanford et al. .......... 435/285.1 |
| 5,501,967 A | 3/1996 | Offringa et al. |
| 5,530,196 A | 6/1996 | Fraley et al. |
| 5,580,722 A | 12/1996 | Foulkes et al. ................. 435/6 |
| 5,610,288 A | 3/1997 | Rubenstein |
| 5,635,381 A | 6/1997 | Hooykaas et al. |
| 5,665,543 A | 9/1997 | Foulkes et al. ................. 435/6 |
| 5,668,295 A | 9/1997 | Wahab et al. ............... 800/205 |
| 5,683,985 A | 11/1997 | Chu et al. ..................... 514/44 |
| 5,684,241 A | 11/1997 | Nakatani et al. ............ 800/205 |
| 5,693,512 A | 12/1997 | Finer et al. |
| 5,713,376 A | 2/1998 | Berger |
| 5,716,780 A | 2/1998 | Edwards et al. ................. 435/6 |
| 5,723,751 A | 3/1998 | Chua |
| 5,731,179 A | 3/1998 | Komari et al. |
| 5,759,829 A | 6/1998 | Shewmaker et al. |
| 5,767,378 A | 6/1998 | Bojsen et al. |
| 5,776,502 A | 7/1998 | Foulkes et al. |
| 5,776,771 A | 7/1998 | Yu et al. |

(Continued)

FOREIGN PATENT DOCUMENTS

| | | |
|---|---|---|
| CA | 2032443 | 12/1990 |
| CA | 2248622 | 9/1998 |
| CA | 2325344 | 4/1999 |
| CA | 1341091 | 9/2000 |
| EP | 0 240 208 B1 | 10/1987 |
| EP | 0 240 208 A3 | 10/1987 |
| EP | 0 265 556 A1 | 5/1988 |
| EP | 0 270 822 A1 | 6/1988 |
| EP | 0 290 799 A3 | 11/1988 |
| EP | 0 290 799 A2 | 11/1988 |
| EP | 0 320 500 A3 | 6/1989 |
| EP | 0 320 500 A2 | 6/1989 |
| EP | 0 647 715 | 3/1990 |
| EP | 0 458 367 A1 | 11/1991 |
| EP | 0 458 367 B1 | 11/1991 |
| EP | 0 467 349 B1 | 1/1992 |
| EP | 0 486 214 A2 | 5/1992 |
| EP | 0 486 214 A3 | 5/1992 |

(Continued)

OTHER PUBLICATIONS

Morishita et al, 1998, Circulation Res. 82:1023–1028.*

Adam et al. (1995) Transcription of tobacco phytochrome–A genes initiates at multiple start sites and requires multiple cis–acting regulatory elements. *Plant Mol. Biol.* 29(5):983–993.

Aparicio et al. (2001) Recognition of cis–acting sequences in RNA 3 of *Prunus necrotic ringspot virus* by the replicase of *Alfalfa mosaic virus*. *J. Gen. Virol.* 82(Pt 4):947–951.

Borisjuk et al. (2000) Tobacco ribosomal DNA spacer element stimulates amplification and expression of heterologous genes. *Nat. Biotechnol.* 18(12): 1303–1306.

(Continued)

*Primary Examiner*—Anne Kubelik
(74) *Attorney, Agent, or Firm*—Myers Bigel Sibley & Sajovec, P.A.

(57) ABSTRACT

The present application describes an isolated promoter fragment that is recognized by the product of the Nic gene of tobacco.

1 Claim, 3 Drawing Sheets

U.S. PATENT DOCUMENTS

| | | |
|---|---|---|
| 5,830,728 A | 11/1998 | Christou et al. |
| 5,834,236 A | 11/1998 | Lamb et al. ............... 435/69.1 |
| 5,837,876 A | 11/1998 | Conkling et al. |
| 5,843,720 A | 12/1998 | Tangney et al. ........... 435/69.1 |
| 5,846,720 A | 12/1998 | Foulkes et al. ................. 435/6 |
| 5,851,804 A | 12/1998 | Snyder et al. |
| 5,858,742 A | 1/1999 | Fraley et al. |
| 5,858,774 A | 1/1999 | Malbon et al. |
| 5,863,733 A | 1/1999 | Foulkes et al. ................. 435/6 |
| 5,877,023 A | 3/1999 | Sautter et al. |
| 5,929,306 A | 7/1999 | Torisky et al. |
| 5,932,782 A | 8/1999 | Bidney |
| 5,962,768 A | 10/1999 | Cornelissen et al. |
| 5,976,793 A | 11/1999 | Foulkes et al. ................. 435/6 |
| 5,976,880 A | 11/1999 | Sautter et al. |
| 5,981,839 A | 11/1999 | Knauf et al. |
| 5,989,915 A | 11/1999 | Christou et al. |
| 5,994,629 A | 11/1999 | Bojsen et al. |
| 6,022,863 A | 2/2000 | Peyman |
| 6,051,409 A | 4/2000 | Hansen et al. |
| 6,051,757 A | 4/2000 | Barton et al. |
| 6,060,310 A | 5/2000 | Cho-Chung ................. 435/375 |
| 6,077,992 A | 6/2000 | Yadav ......................... 800/278 |
| 6,136,779 A | 10/2000 | Foulkes et al. ................. 514/1 |
| 6,165,712 A | 12/2000 | Foulkes et al. ................. 435/6 |
| 6,165,715 A | 12/2000 | Collins et al. |
| 6,174,724 B1 | 1/2001 | Rogers et al. |
| 6,203,976 B1 | 3/2001 | Foulkes et al. ................. 435/6 |
| 6,255,560 B1 | 7/2001 | Fraley et al. |
| 6,262,033 B1 | 7/2001 | Morishita et al. ............. 514/44 |
| 6,271,031 B1 | 8/2001 | Falco et al. |
| 6,281,410 B1 | 8/2001 | Knauf et al. |
| 2001/0006797 A1 | 7/2001 | Kumagai et al. |
| 2001/0026941 A1 | 10/2001 | Held et al. |

FOREIGN PATENT DOCUMENTS

| | | | | |
|---|---|---|---|---|
| EP | 0 486 234 B1 | 5/1992 | | |
| EP | 0 818 532 A1 | 10/1996 | | |
| WO | WO 9012084 | 10/1990 | | |
| WO | WO 9101379 | 2/1991 | | |
| WO | WO 9102070 | 2/1991 | | |
| WO | WO 9111535 | 8/1991 | | |
| WO | WO 9114790 | 10/1991 | | |
| WO | WO 9215680 | 9/1992 | | |
| WO | WO 9218522 | 10/1992 | | |
| WO | WO 9219732 | 11/1992 | | |
| WO | WO 9305163 | 3/1993 | | |
| WO | WO 98/56923 | 4/1993 | ............ | A01H/5/00 |
| WO | WO 93/14768 | 8/1993 | | |
| WO | WO 9314768 | 8/1993 | | |
| WO | WO 9317116 | 9/1993 | | |
| WO | WO 9420627 | 9/1994 | | |
| WO | WO 9426913 | 11/1994 | | |
| WO | WO 9428142 | 12/1994 | | |
| WO | WO 94/28142 | 12/1994 | ............ | C12N/15/54 |
| WO | WO 9511687 | 5/1995 | | |
| WO | WO 95/11687 | 5/1995 | | |
| WO | WO 9512415 | 5/1995 | | |
| WO | WO 9516031 | 6/1995 | | |
| WO | WO 9534668 | 12/1995 | | |
| WO | WO 9535388 | 12/1995 | | |
| WO | WO 9621725 | 7/1996 | | |
| WO | WO 9705261 | 2/1997 | | |
| WO | WO 97/05261 | 2/1997 | | |
| WO | WO 9708330 | 3/1997 | | |
| WO | WO 9712046 | 4/1997 | | |
| WO | WO 9732016 | 9/1997 | | |
| WO | WO 9738723 | 10/1997 | | |
| WO | WO 9741892 | 11/1997 | | |
| WO | WO 9744064 | 11/1997 | | |
| WO | WO 9744450 | 11/1997 | | |
| WO | WO 9749727 | 12/1997 | | |
| WO | WO 9805757 | 2/1998 | | |
| WO | WO 9830701 | 7/1998 | | |
| WO | WO 9832843 | 7/1998 | | |
| WO | WO 93/05646 | 12/1998 | ........... | C12N/15/54 |
| WO | WO 9856923 | 12/1998 | | |
| WO | WO 9910512 | 3/1999 | | |
| WO | WO 9914348 | 3/1999 | | |
| WO | WO 9925854 | 5/1999 | | |
| WO | WO 9926634 | 6/1999 | | |
| WO | WO 9932619 | 7/1999 | | |
| WO | WO 9932642 | 7/1999 | | |
| WO | WO 9949029 | 9/1999 | | |
| WO | WO 9953050 | 10/1999 | | |
| WO | WO 9961631 | 12/1999 | | |
| WO | WO 0012735 | 3/2000 | | |
| WO | WO 0018939 | 4/2000 | | |
| WO | WO 0029566 | 5/2000 | | |
| WO | WO 0037060 | 6/2000 | | |
| WO | WO 0037663 | 6/2000 | | |
| WO | WO 0063398 | 10/2000 | | |
| WO | WO 0067558 | 11/2000 | | |
| WO | WO 0109302 | 2/2001 | | |
| WO | WO 0138514 | 5/2001 | | |
| WO | WO 0144482 | 6/2001 | | |
| WO | WO 0149844 | 7/2001 | | |
| WO | WO 0151630 | 7/2001 | | |
| WO | WO 0168836 | 9/2001 | | |
| WO | WO 0177350 | 10/2001 | | |
| WO | WO 0200927 | 1/2002 | | |

OTHER PUBLICATIONS

Bustos et al. (1989) Regulation of β–glucuronidase expression in transgenic tobacco plants by an A/T–rich. cis–acting sequence found upstream of a French bean β–phaseolin gene. *Plant Cell* 1(9):839–853.

Clusel et al. (1995) Inhibition of HSV–1 proliferation by decoy phosphadiester oligonucleotides containing ICP4 recognition sequences. *Gene Expr.* 4(6):301–309.

Ehsan et al. (2001) Long–term stabilization of vein graft wall architecture and prolonged resistance to experimental atherosclerosis after E2F decoy oligonucleotide gene therapy. *J. Thorac. Cardiovasc. Surg.* 121(4):714–722.

Geffers et al. (2000) Anaerobiosis–specific interaction of tobacco nuclear factors with cis–regulatory sequences in the maize GapC4 promoter. *Plant Mol. Biol.* 43(1):11–21.

Hamill et al. (1990) Over–expressing a yeast ornithine decarboxylase gene in transgenic roots of *Nicotiana rustica* can lead to enhance nicotine accumulation. *Plant Mol. Biol.* 15(1):27–38.

Johnson et al. (2001) Regulation of DNA binding and trans–activation by a xenobiotic stress–activated plant transcription factor. *J. Biol. Chem.* 276(1): 172–178.

Konopka (2000) Rev–binding aptamer and CMV promoter act as decoys to inhibit HIV replication. *Gene* 255(2):235–244.

Morishita et al. (1995) A gene therapy strategy using a transcription factor decoy of the E2F binding site inhibits smooth muscle proliferation in vivo. *Proc. Natl. Acad. Sci. USA* 92(13):5855–5859.

Sharma et al. (1996) Transcription factor decoy approach to decipher the role of NF-$_k$B 13 in oncogenesis. *Anticancer Res.* 16(1):61–19.

Siebertz et al. (1989) *cis*–Analysis of the wound–inducible promoter *wun1* in transgenic tobacco plants and histochemical localization of its expression. *Plant Cell* 1(10):961–968.

Wadgaonkar et al. (1999) CREB–binding protein is a nuclear integrator of nuclear factor–$_\kappa$B and p53 signaling. *J. Biol. Chem.* 274(4):1879–1882.

Wang et al. (1992) Characterization of *cis*–acting elements regulating transcription from the promoter of a constitutively active rice actin gene. *Mol. Cell Biol.* 12(8)3399–3406.

Yamamoto et al. (1991) Characterization of *cis*–acting sequences regulating root–specific gene expression in tobacco. *Plant Cell* 3(4):371–382.

Rafty et al., *Novel Negative Regulator Element in the Platelet–Derived Growth Factor B Chain Promoter That Mediates ERK–Dependent Transcriptional Repression*, The Journal of Biological Chemistry, vol. 275, No. 15, Apr. 14, 2000, pp. 11478–1 1483.

Abeyama et al. "A role for NF–K$_\kappa$B–Dependent Gene Transactivation in Sunburn" *The Journal of Clinical Investigation* 105(12):1751–1759 (Jun. 2000).

Akimoto et al. "Growth Inhibition of Cultured Human Tenon's Fibroblastic Cells by Targeting the E2F Transcription Factor" *Exp. Eye Res.* 67:395–401 (1998).

Beck et al, "Nucleotide Sequence and Exact Localization of the Neomycin Phosphotransferase Gene from Transposon Tn 5". Gene. 19: 327–336(1982).

Bevan & Flavell, "A Chimaeric Antibiotic Resistance Gene as a Selectable Marker for Plant Cell Transformation", Nature, 304: 184–187 (1983).

Burtin, D., et al., *Over expression of Arginine Decarboxylase in Transgenic Plants, Biochem. J.*, vol. 325 (Part 2), pp. 331–337 (1997).

Bush, et al., *Nicotine Biosynthetic Enzymes of Burley Tobacco, Tobacco Abstracts*, vol. 24, p. 260 (1980).

Bush, et al., *Physiological Aspects of Genetic Variation in Nicotine Content in Tobacco (Nicotiana tabacum), Tobacco Abstract*, vol. 23, p. 30 (1979).

Chilton et al., "Tailoring the Agrobacterium Ti Plasmid as a Vector for Plant Genetic Engineering", *Stadler Symp.*, 13: 39–53 (1981).

Colbere–Garapin et al., "A New Dominant Hybrid Selective Marker for Higher Eukaryotic Cells", J. Mol. Biol.. 150: 1–14(1981).

Conkling, et al., *Isolation of transcriptionally regulated root–specific genes from tobacco: Plant Physiology*, vol. 93, No. 3, pp. 1203–1211 (1990).

Cornelissen, et al.. *Both RNA Level and Translation Efficiency are Reduced by Anti–Sense RNA in Transgenic Tobacco, Nucleic Acids Res*, vol. 17. No. 3., pp. 833–843 (1989).

Crowley, et al., *Cell*, "Phenocopy of Discoidin I–Minus Mutants by Antisense Transformation" vol. 43, pp. 633–641 (1985).

Cuozzo. et al., *Viral Protection in Transgenic Tobacco Plants Expressing the Cucumber Mosaic Virus Coat Protein Or Its Antisense RNA, Biotechnology*, vol. 6, pp. 549–557 (1988).

Database entry of Ensembl Human Genome Server, AC006461.2.1.181215, BLASTN 2.0a13MP– WashU [Jun. 10, 1997], 1 pp.

Database entry of Ensembl Human Genome Server, AC069205.6.1.132242, BLASTN 2.0a13MP– WashU [Jun. 10, 1997], 1 pp.

Database entry of Ensembl Human Genome Server, AC097498.3.1.144511, BLASTN 2.0a13MP– WashU [Jun. 10, 1997], 1 pp.

Database entry of Ensembl Human Genome Server. AC105416.3.1.123331, BLASTN 2.0a13MP– WashU [Jun. 10, 1997], 1 pp.

Database entry of Ensembl Human Genome Server, AC108149.3.1.91810, BLASTN 2.0a13MP– WashU [Jun. 10, 1997], 1 pp.

Davis and Jimenez, "A New Selective Agent for Eukaryotic Cloning Vectors", Am. J. Trop. Med. Hyg.. 29(5): 1089–1092 (1980).

D'Acquisto et al. "Local Administration of Transcription Factor Decoy Oligonucleotides to Nuclear Factor–KB Prevents Carrageenin–Induced Inflammation in Rat Hind Paw–"*Gene Therapy* 7:1731–1737 (2000).

Delauney, et al., *A Stable Bifunctional Antisense Transcript Inhibiting Gene Expression in Transgenic Plants, Proc Natl Acad Sci USA*, vol. 85, pp. 4300–4304 (1988).

Depicker et al., "Nopaline Synthase: Transcript Mapping and DNA Sequence", Journal of Molecular and Applied Genetics, 1(6): 561–573 (1982).

Ecker, et al., *Inhibition of Gene Expression in Plant Cells by Expression of Antisense RNA, Proc. Natl Acad Sci USA*, vol. 83 pp. 5372–5376 (1986).

Fraley et al., "Expression of Bacterial Genes in Plant Cells", *Proc Natl Acad Sci* USA, 80: 4803–4807 (1983).

Fraley et al.,"Use of a Chimeric Gene to Confer Antibiotic Resistance to Plant Cells", Advances in Gene Technology: Molecular Genetics of Plants and Animals. 20: 211–221 (1983).

Framond et al., "Mini–Ti: A New Vector Strategy for Plant Genetic Engineering", BIO/TECHNOLOGY, 5: 262–269 (1983).

Genbank entry AB005879. Nicotania tabacum mRNA for BYJ6, Feb. 5, 1999, 2pp.

Genbank entry AC002131. Arabidopsis thaliana chromosome 1 BAC F12F1 sequence, May 28, 1998, 38 pp.

Genbank entry AC006461. Homo sapiens BAC clone RP 11–343N14 from 2, Mar. 1, 2002, 65 pp.

Genbank entry AG024028. Homo sapiens BAC clone RP11–151M24 from 7, Nov. 7, 2001, 68 pp.

Genbank entry AC069205. Homo sapiens BAC clone RP11–735P12 from 2, Jan. 9, 2002, 46 pp.

Genbank entry AC079141. Homo sapiens BAC clone RP11–502A23 from 4, Nov. 7, 2001, 43 pp.

Genbank entry AC115109. Homo sapiens BAC clone RP11–78110 from 2, May 29, 2002, 23 pp.

Genbank entry AR164048. Sequence 7 from patent US 6271031, Oct. 17, 2001. 1 pp.

Genhank entry AR164050. Sequence II From patent US 6271031, Oct. 17, 2001, 1pp.

Genbank entry AX344860. Sequence 285 From patent US WO0200927.Feb. 1, 2002, 4pp.

Genbank entry U27809. Peanut bud necrosis virus S segment non–structural protein and nucleocapsid protein genes, Jul. 23, 1996. 3 pp.

Hamill, et al.; *Over–expressing a yeast ornithine decarboxylase gene in transgenic roots of Nicotiana rustica can lead to enhanced nicotine accumlation, Plant Molecular Biology*, vol. 15, pp. 27–38 (1990).

Hemenway, et al., *Analysis of the Mechanism of Protection in Trasgenic Plants Expressing the Potato Virus x Coat Protein or Its Antisense RNA*, EMBO L. vol. 7. pp. 1273–1280.

Hermaisteens et al., "The Agrobacterium Tumefaciens Ti Plasmid as a Host Vector System for Introducing Foreign DNA in Plant Cells", Nature, 287: 654–656 11980).

Herrera–Estrella et al., "Chimeric Genes as Dominant Selectable Markers in Plant Cells", The Embo Journal, 2(6): 987–995 (1993).

Herrera–Estrella et al., "Expression of Chimaerie Genes Transferred into Plant Cells Using a Ti–Plasmid–Derived Vector", Nature. 303: 209–213 (1983).

Hibi, et al., *Gene Expression in Tobacco Low–Nicotine Mutants*, Plant Cell, vol. 6, pp. 723–735 (1994).

Holmberg, et al.; *Transgenic tobacco expressing Vitreoscilla hemoglobin exhibits enhanced growth and altered metabolite production*, Nature Biotechnology, vol. 15, pp. 244–247 (1997).

Hooykaas et al., "The Ti–Plasmid of Agrobacterium Tumefaciens: A Natural Genetic Engineer", TIBS,307–309 (1985).

Horsch et al., "A Simple and General Method for Transferring Genes into Plants", Biological Sciences, 227: 1229–1231 (1985).

Hughes, Kelly T., et al., *The Salmonella typhimurium nadC Gene: Sequence Determination by Use of Mud–P22 and Purification of Quinolinate Phosphoribosyltransferase*, Journal of Bacteriology, vol. 175. No. 2, pp. 479–486 (Jan. 1993).

Imanishi et al., "Differential Induction by Methyl Jasmonate of Genes Encoding Ornithine Decarboxylase and Other Enzymes Involved in Nicotine Biosynthesis in Tobacco Cell Cultures", Plant Molecular Biology, 38: 1101–1111 (1998).

Izant, et al., *Constitutive and conditional Suppression of Exogenous and Endogenous Genes by Anti–Sense RNA*, Science, vol. 229, pp. 345–352 (1985).

Izant, et al., *Inhibition of Thymidine Kinase Gene Expression by Anti–Sense RNA: A Molecular Approach to Genetic Analysis*, Cell, vol. 36, pp. 1007–1015 (Apr. 1984).

Kim, et al., *Stable Reduction of Thymidine Kinase Activity in Cells Expressing High Levels of Anti–Sense RNA*, Cell, vol. 42, pp. 129–138 (Aug. 1985).

Kitamoto et al. "Increased Activity of Nuclear Factor–κB Participates in Cardiovascular Remodeling Induced by Chronic Inhibition of Nitric Oxide Synthesis in Rats" *Circulation* 102:806–812 (2000).

Kubota, et al. "Cloning of a Nuclear–Encoded Photosystem I Gene, *psaEb*, in *Nicotiana sylvestris*" Plant Physiol 108:1297–1298 (1995).

Lam, et al., *Site–Specific Mutations Alter In Vitro Factor Binding and Change Promoter Expression Pattern in Transgenic Plants*, Proc. Nat. Acad. Sci. USA, vol. 86, pp. 7890–7894 (1989).

Lee et al. "CRE–Transcription Factor Decoy Oligonucleotide Inhibition of MCF-7 Breast Cancer Cells: Cross–Talk with p53 Signaling Pathway" *Biochemistry* 39:4863–4868 (2000).

Lichtenstein, *Anti–sense RNA As A Tool To Study Plant Gene Expression*, Nature, vol. 333, pp. 801–802 (1988).

Lorz et al., "Transformation Studies Using Synthetic DNA Vectors Coding For Antibiotic Resistance", Plant Tissue Culture. 511–512 (1982).

Mann et al. "Pressure–Mediated Oligonucleotide Transfection of Rat and Human Cardiovascular Tissues" *Proc Nail Acad Sci USA: Medical Sciences* 96:6411–6416 (May 1999).

Mann et al. "Ex–vivo Gene Therapy of Human Vascular Bypass Grafts with E2F Decoy: The PREVENT Single–Centre, Randomised, Controlled Trial" *The Lancet* 354:1493–1498 (Oct. 30, 1999).

MeGarry, et al., "Inhibition of Heat Shock Protein Synthesis by Heat–Inducible Antisense RNA" *Proc. Natl. Acad. Sci. USA* 83:399–403 (1986).

Melton, *Injected Anti–Sense RNAs .Specifically Block Messenger RNA Translaton In Vivo*, Proc. Natl Acad Sci USA, vol. 82, pp. 144–148 (1985).

Mischiati et al. "Interaction of the Human NF–κB p52 Transcription Factor with DNA–PNA Hybrids Mimicking the NF–κB Binding Sites of the Human Immunodeficiency Virus Type I Promoter" *The Journal of Biological Chemistry* 274(46):33114–33122 (1999).

Mizuno, et al., *A Unique Mechanism Regulating Gene Expression: Translational Inhibition By a Complementary RNA Transcript (micRNA)*, Trends in Genetics, vol. 1. pp. 22–25 (1985).

Morishita, et al. "Role of AP–1 Complex in Angiotensin II–Mediated Transforming Growth Factor–β Expression and Growth of Smooth Muscle Cells: Using Decoy Approach Against AP–1 Binding Site" *Biochemical and Biophysical Research Communications* 243:361–367 (1998).

Morishita, et al. "Application of Transcription Factor "Decoy" Strategy as Means of Gene Therapy and Study of Gene Expression in Cardiovascular Disease" *Circ. Res.* 82:1023–1028 (1998).

Nastruzzi et al. "Liposomes as Carriers for DNA–PNA Hybrids" *Journal of Controlled Release* 68:237–249 (2000).

Ohta, et al., *Metabolic Key Step Discriminating Nicotine Producing Tobacco Callus Strain From Ineffective One.* Biochem. Physiolo Pflanzen, vol. 175, pp. 382–385 (1980).

Park et al. "Dual Blockade of Cyclic AMP Response Element–(CRE) and AP–a–Directed Transcription by CRE–Transcription Factor Decoy Oligonucleotide" *The Journal of Biological Chemistry* 274(3):1573–1580 (Jan. 15, 1999).

Pestka, et al., *Anti–mRNA: Specific Inhibition of Translation of Single mRNA Molecules*, Proc. Natl. Acad. Sci. USA, vol. 81, pp. 7525–7528 (1984).

Piva et al. "Modulation of Estrogen Receptor Gene Transcription in Breast Cancer Cells by Liposome Delivered Decoy Molecules" *Journal of Steroid Biochemistry and Molecular Biology* 75:121–128 (2000).

Poulsen, et al., *Dissection of 5' Upstream Sequences for Selective Expression of the Nicotiana, Plubaginifolia rbcS–8B gene*, Mol. Gen. Genet, vol., 214, pp. 16–23 (1988).

Preiss, et al., *Molecular genetics of Krüppel, A Gene Required for Segmentation of the Drosphila Embryo*, Nature, vol. 313(5997):27–32 (1985).

Rezaian, et al., *Anti–Sense RNAs of Cucumber Mosaic Virus in Transgenic Plants Assessed For Control of the Virus*, Plant Molecular Biology. vol. 11, pp. 463–471 (1988).

Rodermel. et al., *Nuclear–Organelle Interactions: Nuclear Antisense Gene Inhibits Ribulose Biphosphate Carboxylase Enzyme Levels In Transformed Tobacco Plants*, Cell, vol. 55, pp. 673–681 (1988).

Rosenberg, et al., *Production of Phenocopies by Krüppel Antisense RNA Injection Into Drosophila Embryos.* Nature, vol. 313, pp. 703–706 (1985).

Rothstein. et al.. *Stable and Heritable Inhibition of the Expression of Nopaline Synthase in Tobacco Expressing Antisense RNA*, Proc. Natl. Sci. USA, vol. 84. pp. 8439–8443 (1987).

Sandler, et al., *Inhibition of Gene Expression in Transformed Plants by Antisense RNA*, Plant Molecular Biology, vol. 11, pp. 301–310 (1988).

Saunders, et al., *Comparison of Nicotine Biosynthetic Enzymes in Nicotine Level Genotypes of Burley Tobacco*, Agronomy Abstracts, p. 84 (1978).

Saunders, et al., *Enzyme Activities in Nicotine Biosynthesis in Nicotiana Tabacum*, Journal of National Products, vol. 41, p. 646.

The Sanger Centre, "Toward a Complete Human Genome Sequence", Cold Spring Harbor Laboratory Press, 1097–1108, (1988).

Satyanarayana et at., "Peanut Bud Necrosis Tospovirus S RNA : Complete Nucleotide Sequence, Genome Organization and Homology to Other Tospoviruses", Arch. Virol. 141 (1), 85–98 (1996).

Sheehey, et al., *Reduction of Polygalacturonase Activity in Tomato Fruit by Antisense RNA;* Proc. Natl. Acad. Sci. USA, vol. 85, pp. 8805–8809 (1988).

Smith et al., "Antisense RNA Inhibition of Polygalacturonase Gene Expression in Transgenic Tomatoes", Nature, 334: 724–726(1988).

Song, Wen, *Molecular characterizations of two tobacco root–specific genes: TobRB7 and NiOPTI(1997); UMI*, Order No. DA9804246 from: Diss. Abstr. Int.. B. vol. 58, No. 8, p. 4061; 224 pp. available; XP002080228.

Takata, et al. "Novel *Cis* Element for Tissue–Specific Transcription of Rat Platelet–Derived Growth Factor β–Receptor Gene" Hypertension 33(II):298–302 (1999).

Theologis et al., "Sequence and Analysis of Chromosome 1 of the Plant Arabidopsis Thaliana", Nature, 408: 816–820(2000).

Tomita, et al. "Transcription Factor Decoy for NF B Inhibits Cytokine and Adhesion Molecule Expressions in Synovial Cells Derived from Rheumatoid Arthritis" Rheumatology 39:749–757 (2000).

Travers, *Regulation by Anti–Sense RNA*, Nature, vol. 310, p. 410 (1984).

Van der Krol, et al., *An Anti–Sense Chalcone Synthase Gene in Transgenic Plants Inhibits Flower Pigmentation*, Nature, vol. 333, pp. 866–869 (1988).

Van der Krol, et al., *Antisense Genes in Plants; An Overview*, Gene, vol. 72, pp. 45–50 (1988).

Van der Krol, et al., *Modulation of Eukaryotic Gene Expression by Complementary RNA or DNA Sequences*, Biotechniques, vol. 6, pp. 958–976 (1988).

Wang et al., "Right 25 bp Terminus Sequence of the Nopaline T– DNA is Essential for and Determines Direction of DNA Transfer from Agrobacterium to the Plant Genome", Cell, 38: 455–462 (1984).

Wang, et al. "Targeted Disruption of Stat6 DNA Binding Activity by an Oligonucleotide Decoy Blocks IL–4–Driven $T_H2$ Cell Response" Blood 95(4): 1249–1257 (Feb. 15, 2000).

Wagner, et al., *Regulation in Tobacco Callus of Enzyme Activities of the Nicotine Pathway*, Planta, vol. 168, pp. 408–412. (1986).

Wagner, et al., *The Regulation of Enzyme Activities of the Nicotine Pathway in Tobacco*, Physiol. Plantarum, vol. 68, pp. 667–672 (1986).

Wagner et al. "Determination of Quinolinic Acid Phosphoriboxyl–Transferase in Tobacco" Phytochemistry 23(9):1881–1883 (1984).

Watanabe et al. "Cloning and Expression of Two Genes Encoding Auxin–Binding Proteins From Tobacco" Plant Molecular Biology 36:63–74 (1998).

Weintraub, et al., *Anti–sense RNA as a Molecular Tool for Genetic Analyis*, Trends in Genetics, vol. 1, pp. 22–25 (1985).

West, et al., *Duplex–Duplex Interactions Catalyzed by RecA Protein Allow Strand Exchanges to Pass Double–Strand Breaks in DNA*, Cell, pp. 683–691 (1984).

Wu et al. "Inhibition of In Vitro Transcription by Specific Double–Stranded Obligodeoxyribonucleotides" Gene 89:203–209 (1990).

Yia–Herttuala et al. "Cardiovascular Gene Therapy" The Lancet 355:213–222 (Jan. 15, 2000).

* cited by examiner

SEQUENCE LISTING

<160> NUMBER OF SEQ ID NOS: 4

<210> SEQ ID NO 1
<211> LENGTH: 456
<212> TYPE: DNA
<213> ORGANISM: Nicotiana tabacum

<400> SEQUENCE: 1
ggaaacatat tcaatacatt gtagtttgct actcataatc gctagaatac tttgtgcctt      60
gctaataaag atacttgaaa tagcttagtt taaatataaa tagcataata gattttagga     120

-continued

| | | |
|---|---|---|
| attagtattt tgagtttaat tacttattga cttgtaacag tttttataat tccaaggccc | 180 |
| atgaaaaatt taatgcttta ttagttttaa acttactata taaattttc atatgtaaaa | 240 |
| tttaatcggt atagttcgat attttttcaa tttattttta taaaataaaa aacttaccct | 300 |
| aattatcggt acagttatag atttatataa aaatctacgg ttcttcagaa gaaacctaaa | 360 |
| aatcggttcg gtgcggacgg ttcgatcggt ttagtcgatt ttcaaatatt cattgacact | 420 |
| cctagttgtt gttataggta aaaagcagtt acagag | 456 |

<210> SEQ ID NO 2
<211> LENGTH: 13
<212> TYPE: DNA
<213> ORGANISM: Artificial sequence
<220> FEATURE:
<223> OTHER INFORMATION: Synthetic oligonucleotide

<400> SEQUENCE: 2
ggtagtaagg tag                                              13

<210> SEQ ID NO 3
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 3
gccacctcaa                                                  10

<210> SEQ ID NO 4
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 4
cacacgtcaa                                                  10

PROMOTER FRAGMENT THAT IS RECOGNIZED BY THE PRODUCT OF THE TOBACCO *NIC* GENE

RELATED APPLICATIONS

This application claims the benefit of provisional application Ser. No. 60/229,198, filed Aug. 30, 2000, the disclosure of which is incorporated by reference herein in its entirety.

FIELD OF THE INVENTION

The present invention describes a process for the production of transgenic plants such as transgenic tobacco plants with altered protein content therein, leading to altered phenotypes such as reduced nicotine levels, along with transgenic plants so produced and seed for such plants.

BACKGROUND OF THE INVENTION

The production of tobacco with decreased levels of nicotine is of interest, given concerns regarding the addictive nature of nicotine. Additionally, tobacco plants with extremely low levels of nicotine production, or no nicotine production, are attractive as recipients for transgenes expressing commercially valuable products such as pharmaceuticals, cosmetic components, or food additives. Various processes have been designed for the removal of nicotine from tobacco. However, most of these processes remove other ingredients from tobacco in addition to nicotine, thereby adversely affecting the tobacco. Classical crop breeding techniques have produced tobacco plants with lower levels of nicotine (approximately 8%) than that found in wild-type tobacco plants. Tobacco plants and tobacco having even further reductions in nicotine content are desirable.

Nicotine is formed primarily in the roots of the tobacco plant and is subsequently transported to the leaves, where it is stored (Tso, *Physiology and Biochemistry of Tobacco Plants*, pp. 233–34, Dowden, Hutchinson & Ross, Stroudsburg, Pa. (1972)). Nicotine is produced by the condensation of two precursors, nicotinic acid and N-methylpyrolinium, that arise from two separate biosynthetic pathways (see FIG. 1)(Bush and Saunders (1977) *Proc. Am. Chem. Soc. Symp.*, New Orleans, pp. 389–425; Hashimoto and Yamada (1994) *Annu. Rev. Plant Physiol. Plant Mol. Biol.* 45, 257–285; Waller and Dermer (1981) In: *The Biochemistry of Plants: A Comprehensive Treatise*, P. K. Stumpf and E. E. Conn, eds. Academia Press, pp. 317–395). The pyridine nucleotide cycle synthesize nicotinic acid (Wagner et al. (1986) *Planta* 167, 226–232; Wagner and Wagner (1985) *Planta* 165, 532–537), whereas N-methylpyrrolinium cations are synthesized from ornithine or arginine via putrescence (Leete (1980) In: *Encyclopedia of Plant Physiology, Secondary Plant Products*, Vol. 8, E. A. Bell and B. V. Charlwood, eds, Springer-Verlag, pp. 65–91; Tiburcio and Galston (1986) *Phytochemistry*, 25, 107–110). Reciprocal grafting experiments have demonstrated that nicotine is synthesized in roots and transported through the xylem to leaves and other plant organs (Dawson (1941) *Science*, 94, 396–397).

Two regulatory loci (Nic1 and Nic2) regulate nicotine production. Legg et al. ((1969) *J. Hered.*, 60, 213–217) incorporated genes from low alkaloid content Cuban cigar cultivars into Burley 21 cultivars. These investigators showed that the low alkaloid lines differed from standard cultivars at two loci, Nic1 (formerly identified as A) and Nic2 (formerly identified as B). These two loci are unlinked and the gene action is semi-dominant and primarily additive (Legg et al. (1969) *J. Hered.*, 60, 213–217). Collins et al. ((1974) *Crop Sci.*, 14, 77–80) prepared doubled haploid tobacco breeding lines of these four alkaloid genotypes. The genotype of standard cultivars is Nic1/Nic1 Nic2/Nic2 and that of low nicotine lines is nic1/nic1 nic2/nic2. Nic1/Nic1 nic2/nic2 is a high intermediate and nic1/nic1 Nic2/Nic2 is a low intermediate (Legg and Collins (1971) *Can. J. Genet. Cytol.* 13, 287–291). These lines are similar in days-to-flower, number of leaves, leaf size, and plant height. Enzyme analyses of roots of single and double Nic mutants show that the activities of two enzymes, quinolinate phosphoriboxyl transferase (QPTase) and putrescence methyl transferase (PMTase), are directly proportional to levels of nicotine biosynthesis (Saunders and Bush (1979) *Plant Physiol* 64:236). Both Nic1 and Nic2 affect PMTase and QPTase activities in roots, and thus, regulate nicotine synthesis (Leete (1983) In: *Alkaloids: Chemical and Biological Perspectives*, S. W. Pelletier, ed. John Wiley & Sons, pp. 85–152).

Hibi et al. ((1994) *Plant Cell*, 6, 723–735) isolated the cDNA encoding PMTase, PMT, and showed that PMT transcript levels are regulated by Nic1 and Nic2. The QPTase cDNA and genomic clones (NtQPT1) have also been isolated and the transcript levels of NtQPT1 are also regulated by Nic1 and Nic2 (Song, W., Mendu, N., and Conkling, M. A. (1999) *Plant Cell*, in preparation). Thus, it appears that the Nic genes regulate nicotine content by regulating the transcript levels of genes encoding the two rate-limiting enzymes, PMTase and QPTase. Further, Nic1 and Nic2 have been shown to be positive regulators of NtQPT1 transcription and that promoter sequences upstream of the transcription initiation site contain the cis-acting sequences necessary for Nic gene product activation of NtQPT1 transcription. Because expression of QPTase and PMTase are coordinately-regulated by the Nic gene products, it likely that the Nic gene products also directly regulate transcription of the PMT gene.

One approach for reducing the level of a biological product, such as nicotine, is to reduce the amount of a required enzyme (i.e. QPTase and PMTase) in the biosynthetic pathway leading to that product. Where the affected enzyme naturally occurs in a rate-limiting amount (relative to the other enzymes required in the pathway), any reduction in that enzyme's abundance will decrease the production of the end product. If the amount of the enzyme is not normally rate-limiting, its presence in a cell must be reduced to rate-limiting levels in order to diminish the pathway's output. Conversely, if the naturally-occurring amount of enzyme is rate limiting, then any increase in the enzyme's activity will result in an increase in the biosynthetic pathway's end product. The modification of nicotine levels in tobacco plants by antisense regulation of putrescence methyl transferase (PMTase) expression is proposed in U.S. Pat. Nos. 5,369,023 and 5,260,205 to Nakatani and Malik. PCT application WO 94/28142 to Wahad and Malik describes DNA encoding PMT and the use of sense and antisense PMT constructs. Additionally, PCT Application WO98/56923 to Conkling et al. describes DNA encoding a plant quinolate phosphoribosyl transferase (QPRTase) enzyme, constructs comprising such DNA, and methods of altering QPRTase expression to increase or decrease nicotine production in plants. Despite previous efforts and successes, there remains a need for new approaches to reduce the production of gene products in plants (e.g., nicotine).

SUMMARY OF THE INVENTION

A first aspect of the present invention is an isolated nucleic acid molecule (e.g., a plasmid) comprising, consisting essentially of, or consisting of a cis-acting regulatory element, and the use of such an isolated nucleic acid for the production of a transgenic plant or host cell having altered levels (e.g., increased or decreased levels) of a protein of interest therein. A particular example is a Nic gene product responsive element (e.g., a DNA sequence that binds to a Nic gene product) such as (a) isolated nucleic acids having a sequence according to SEQ ID NO: 1 or a fragment thereof consisting essentially of or consisting of, desirably, at least 20–455 consecutive nucleotides, preferably, at least 30–400 consecutive nucleotides, more preferably, 50–350 consecutive nucleotides, and, most preferably, 100–300 or 200–400 consecutive nucleotides; and (b) isolated nucleic acids that hybridize to the complement of SEQ ID NO:1 and bind or are otherwise responsive to a Nic gene product (i.e. increase or decrease transcription of an operatively associated gene and hence increase or decrease the level of the encoded protein of interest in the host cells).

The Nic gene product responsive element can also be obtained from the sequence disclosed in U.S. Pat. No. 5,459,252, herein expressly incorporated by reference in its entirety. In some embodiments, the Nic gene product responsive element resides between −1000 and −600 or −700 bp of the NtQPT1 promoter, the sequence of which is disclosed in U.S. Pat. No. 5,459,252. Accordingly, some embodiments involve a 300–400 nucleotide long fragment of the NtQPT1 promoter that corresponds to the sequence of the NtQPT1 promoter between −1000 and −600 or −700, as disclosed in U.S. Pat. No. 5,459,252.

A second aspect of the present invention is a recombinant nucleic acid construct comprising containing a cis-acting regulatory element such as a Nic gene product responsive element as described above, along with the use of such a recombinant nucleic acid for the production of a transgenic plant or host cell as described herein. The construct may be a vector, such as a ballistic nucleic acid transfer particle or an *Agrobacterium* vector. Plant cells containing such constructs, and preferably multiple copies thereof, are also an aspect of the invention.

A further aspect of the present invention is a method of making a transgenic tobacco plant having reduced nicotine content and/or tobacco specific nitrosamines (TSNA)s. The method comprises introducing an exogenous nucleic acid construct comprising a Nic gene product responsive element as described above into said at least one tobacco plant cell to produce at least one transformed tobacco plant cell. The at least one transformed tobacco plant cell contains the exogenous nucleic acid in an amount or copy number sufficient to reduce the nicotine and/or TSNA level of a tobacco plant regenerated from that cell or cells as compared to the nicotine and/or TSNA level that would be present in the absence of the exogenous nucleic acid. The method may further include generating a tobacco plant from the transformed plant cells, and (optionally) collecting tobacco leaves, stems, or seed from the tobacco plant. Thus, tobacco plants, including the leaves, stems, and seeds, generated from said method are also aspects of the present invention.

A further aspect of the present invention is a tobacco plant having reduced levels of nicotine and/or TSNAs therein, the plant comprising cells containing an exogenous nucleic acid, which exogenous nucleic acid comprises a Nic gene product responsive element as described above. The exogenous nucleic acid is contained in the cells in a copy number sufficient to reduce the nicotine level of that tobacco plant as compared to the nicotine level that would be present in that plant in the absence of the exogenous nucleic acid. Again, the leaves, stems, and seeds of such plant are also aspects of the present invention.

Tobacco products including, but not limited to, smoking materials (e.g., cigarettes, cigars, pipe tobacco), snuff, chewing tobacco, gum, lozenges that are prepared from said transgenic tobacco plants are also embodiments of the invention. Preferably these tobacco products are manufactured from harvested tobacco leaves and stems that have been cut, dried, cured, and/or fermented according to conventional techniques in tobacco preparation. However, modified techniques in curing and tobacco processing can also be implemented to further lower the levels of TSNAs. In some embodiments, the tobacco that is made substantially free of nicotine and/or TSNAs is prepared from a variety of Burley tobacco (e.g., Burley 21), Oriental tobacco, or Flue-cured tobacco. It should be understood, however, that most tobacco varieties can be made to be nicotine and/or TSNA free using the embodiments described herein.

Additional embodiments include tobacco products that have been carefully blended so that desired levels of nicotine and/or TSNAs are obtained. For example, tobacco having a reduced level of nicotine and/or TSNAs, prepared as described above, can be blended with conventional tobacco so as to obtain virtually any amount of nicotine and/or TSNAs. Further, two or more varieties of tobacco having a reduced level of nicotine and/or TSNAs can be blended so as to achieve a desired amount of nicotine and/or TSNAs. In this manner, differences in variety, flavor, as well as amounts of nicotine and/or TSNAs can be incrementally adjusted. These blended tobacco products can be incorporated into tobacco use cessation kits and programs designed to reduce or eliminate nicotine dependence and carcinogenic potential. Such kits and programs are also embodiments of the invention.

More embodiments of the invention concern methods to reduce the carcinogenic potential of tobacco products, including cigarettes, cigars, chewing tobacco, snuff and tobacco-containing gum and lozenges. Some methods, for example involve the preparation of tobacco having a reduced amount of nicotine and/or TSNAs and the manufacture of tobacco products containing said tobacco. Accordingly, the transgenic tobacco plants, described above, are harvested, cured, and processed into tobacco products. These tobacco products have a reduced carcinogenic potential because they are prepared from tobacco that has a reduced amount of nicotine and/or TSNAs.

Yet another aspect of the invention concerns the reduction of the amount of TSNAs and metabolites thereof in humans who smoke, consume or otherwise ingest tobacco. This method is practiced by providing a tobacco product having a reduced amount of TSNAs, as described above, to said humans, thereby lowering the carcinogenic potential of such product in said humans.

More generally, the present invention provides a method of making a plant having increased or reduced content of a protein of interest therein, wherein the protein of interest is regulated by a cis-acting element selected from the group consisting of (i) a cis-acting activating element that binds an activator compound, which activator compound increases expression of said protein of interest in said plant, and (ii), a cis-acting repressor element that binds a repressor compound, which repressor compound decreases expression of said protein of interest in said plant. The method comprises introducing an exogenous nucleic acid construct comprising said cis-acting element into at least one plant cell to produce at least one transformed plant cell, with the at least one transformed plant cell containing the exogenous nucleic acid in a copy number sufficient to increase or reduce the level of said protein of interest in a plant regenerated from said cells as compared to the amount of said protein of interest that would be present in the absence of said exogenous nucleic acid.

The present invention thus generally provides a plant (and parts thereof) having increased or reduced levels of a protein of interest therein, the plant comprising cells containing an exogenous nucleic acid, which exogenous nucleic acid comprises a cis-acting element selected from the group consisting of (i) a cis-acting activating element that binds an activator compound, which activator compound increases expression of said protein of interest in said plant, and (ii), a cis-acting repressor element that binds a repressor compound, which repressor compound decreases expression of said protein of interest in said plant; the cells containing the exogenous nucleic acid in a copy number sufficient to increase or reduce the level of the protein of interest in the plant as compared to the amount of the protein of interest that would be present in the absence of the exogenous nucleic acid.

Thus the present invention provides a general method of decreasing expression of a protein of interest in a (prokaryotic or eukaryotic) host cell, wherein transcription of the protein of interest is enhanced by a cis-acting activating element that binds an activator compound, which activator compound increases expression of the protein of interest in the host cell. The method comprises the steps of: (a) providing a decoy recombinant nucleic acid construct comprising the cis-acting activating element; and (b) introducing the decoy construct into the host cell in an amount sufficient to bind the activator compound and reduce expression of the protein of interest.

Further, the present invention provides a general method of increasing expression of a protein of interest in a host cell, wherein transcription of the protein of interest is reduced by a cis-acting repressor element that binds a repressor compound, which repressor compound reduces expression of said protein of interest in said host cell. The method comprises the steps of: (a) providing a decoy recombinant nucleic acid construct comprising said cis-acting activating element; and (b) introducing said decoy construct into said host cell in an amount sufficient to bind said repressor compound and increase expression of said protein of interest.

The foregoing and other aspects of the present invention are explained in greater detail in the drawings herein and the specification set forth below.

DETAILED DESCRIPTION OF THE PREFERRED EMBODIMENT

Figure 1:
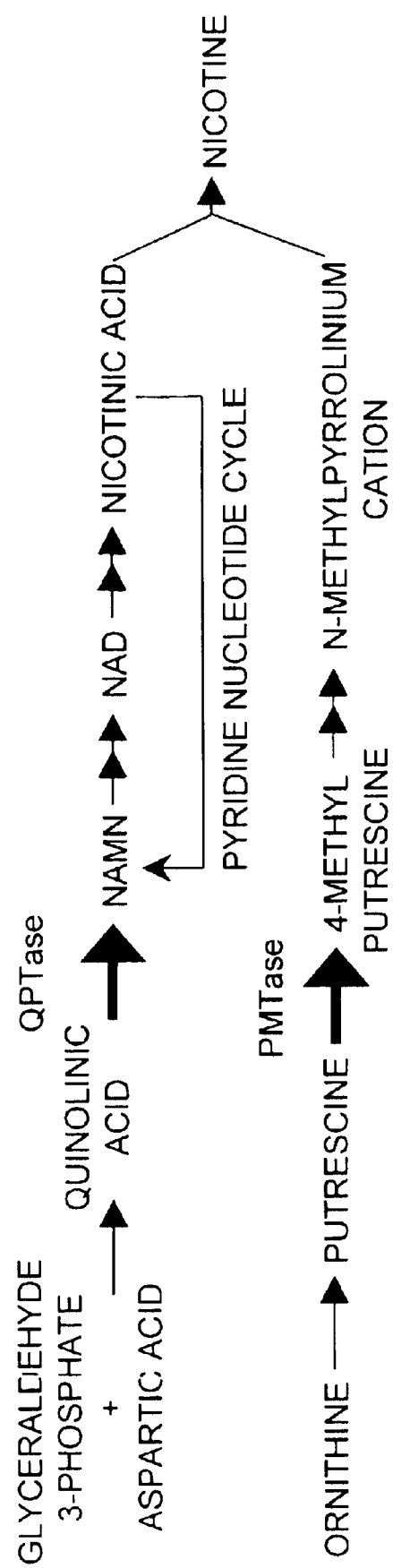
FIG. 1 depicts the biosynthetic pathway leading to nicotine biosynthesis. Enzyme activities known to be regulated by Nic1 and Nic2 are QPTase (quinolinate phosphoribosyl transferase) and PMTase (putrescence methyl-transferase). QPTase and PMTase are the rate-limiting enzymatic steps in nicotine biosynthesis and thus, nicotine levels are directly proportional to the QPTase and PMTase activities.

The term "plants" as used herein refers to vascular plants. Exemplary plants include, but are not limited to, corn (*Zea mays*), canola (*Brassica napus, Brassica rapa* ssp.), alfalfa (*Medicago saliva*), rice (*Oryza sativa*), rape (*Brassica napus*), rye (*Secale cereale*), sorghum (*Sorghum bicolor, Sorghum vulgare*), sunflower (*Helianthus annus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*), duckweed (*Lemna*), oats, barley, vegetables, ornamentals, conifers, and turfgrasses (e.g., for ornamental, recreational or forage purposes). Vegetables include Solanaceous species (e.g., tomatoes; *Lycopersicon esculentum*), lettuce (e.g., *Lactuea sativa*), carrots (*Caucus carota*), cauliflower (*Brassica oleracea*), celery (*apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus *Cucurbita* such as Hubbard squash (*C. Hubbard*), Butternut squash (*C. moschata*), Zucchini (*C. pepo*), Crookneck squash (*C. crookneck*), *C. argyrosperma, C. argyrosperma* ssp *sororia, C. digitata, C. ecuadorensis, C. foetidissima, C. lundelliana*, and *C. martinezii*, and members of the genus *Cucumis* such as cucumber (*Cucumis sativus*), cantaloupe (*C. cantalupensis*), and musk melon (*C. melo*). Ornamental plants include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), *petunias* (*Petunia hybrida*), carnation (*Dianthus caryophyllus*), poinsettia (*Euphorbia pulcherima*), and chrysanthemum. Conifers, which may be employed in practicing the present invention, include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Turfgrass include but are not limited to zoysiagrasses, bentgrasses, fescue grasses, bluegrasses, St. Augustinegrasses, bermudagrasses, buffalograsses, ryegrasses, and orchardgrasses. Also included are plants that serve primarily as laboratory models, e.g., *Arabidopsis*. Preferred plants for use in the present methods include (but are not limited to) legumes, solanaceous species (e.g., tomatoes), leafy vegetables such as lettuce and cabbage, turfgrasses, and crop plants (e.g., tobacco, wheat, *sorghum*, barley, rye, rice, corn, cotton, cassava, and the like), and laboratory plants (e.g., *Arabidopsis*). While any plant may be used to carry out the present invention, tobacco plants are particularly preferred.

Plant parts that can be collected from the plants of the present invention (e.g., cut or harvested) include, for example, fruits, flowers, seed, roots, tubers, leaves, stems, bark, wood, etc. Note that when reference is made to a particular protein being increased or reduced in a plant, the amount of that protein may be altered throughout the plant, or only in a particular part of the plant.

In overview, in an illustrative embodiment of the invention, nicotine is produced in tobacco plants by the condensation of nicotinic acid and N-methylpyrrolinium cation. The biosynthetic pathway resulting in nicotine production is illustrated in FIG. 1. Two regulatory loci (Nic1 and Nic2) act as co-dominant regulators of nicotine production. Enzyme analyses of roots of single and double Nic mutants show that the activities of two enzymes, quinolate phosphoribosyl transferase (QPTase) and putrescence methyl transferase (PMTase), are directly proportional to levels of nicotine biosynthesis. A comparison of enzyme activity in tobacco tissues (root and callus) with different capacities for nicotine synthesis shows that QPTase and PMTase activity are strictly correlated with nicotine content (Wagner and Wagner, *Planta* 165:532 (1985)). Saunders and Bush (*Plant Physiol* 64:236 (1979) showed that the level of QPTase in the roots of low nicotine mutants is proportional to the levels of nicotine in the leaves.

The present invention is, in one preferred embodiment, based upon an isolated nucleic acid (e.g., SEQ ID NO:1 or a fragment thereof consisting of, desirably, at least 20–450 consecutive nucleotides, preferably, at least 30–400 consecutive nucleotides, more preferably, 50–350 consecutive nucleotides, and, most preferably, 100–300 or 200–400 consecutive nucleotides) that is or contains at least one cis-acting regulatory element, which exists upstream of the plant quinolate phosphoribosyl transferase (QPTase) and putrescence methyl transferase (PMTase) coding sequences. Another example is the Nic gene product responsive element obtained from the sequence disclosed in U.S. Pat. No. 5,459,252, herein expressly incorporated by reference in its entirety. In some embodiments, the Nic gene product responsive element resides between –1000 and –600 or –700 bp of the NtQPT1 promoter. Accordingly, some embodiments involve a 300–400 nucleotide long fragment of the NtQPT1 promoter that corresponds to the sequence of the NtQPT1 promoter between –1000 and –600 or –700, as disclosed in U.S. Pat. No. 5,459,252.

Thus, in some embodiments, the embodied nucleic acids have a structure that promotes an interaction with one or more transcription factors (e.g., Nic1 and Nic2), which are involved in initiating transcription of QPTase and/or PMTase. Accordingly, said nucleic acids are said to be or contain at least one transcription factor (e.g., Nic1 and Nic2) binding sequences, which are also referred to as "cis-acting regulatory elements." By introducing multiple copies of these cis-acting regulatory elements (e.g., sequences that interact with Nic1 and/or Nic2) into a plant cell, the ability of the transcription factor to initiate transcription of the targeted gene (e.g., QPTase and/or PMTase genes) can be reduced or squelched.

As QPTase and PMTase activities are strictly correlated with nicotine content, construction of transgenic tobacco plants in which QPTase or PMTase levels are lowered in the plant roots (compared to levels in wild-type plants), as decribed above, result in plants having reduced levels of nicotine. Without wishing to be bound by any particular theory, it is contemplated that the creation of tobacco plants, tobacco, and tobacco products that have a reduced amount of nicotine will also have a reduced amount of TSNA. That is, by removing nicotine from tobacco plants, tobacco, and tobacco products, one effectively removes the alkaloid substrate for TSNA formation. It was found that the reduction of nicotine in tobacco was directly related to the reduction of TSNAs. Unexpectedly, the methods described herein not only produce tobacco with a reduced addictive potential but, concomitantly, produce a tobacco that has a lower carcinogenic potential.

It should be emphasized that the phrase "a reduced amount" is intended to refer to an amount of nicotine and or TSNA in a transgenic tobacco plant, tobacco, or a tobacco product that is less than what would be found in a tobacco plant, tobacco, or a tobacco product from the same variety of tobacco processed in the same manner, which was not made transgenic for reduced nicotine and/or TSNA. Thus, in some contexts, wild-type tobacco of the same variety that has been processed in the same manner is used as a control by which to measure whether a reduction in nicotine and/or TSNA has been obtained by the inventive methods described herein.

Wild type tobacco varies significantly in the amount of TSNAs and nicotine depending on the variety and the manner it is grown, harvested, and cured. For example, a Burley tobacco leaf has 30,000 parts per million (ppm) nicotine and 8,000 parts per billion (ppb) TSNA; a Flue-Cured Burley leaf has 20,000 ppm nicotine and 300 ppb TSNA; and an Oriental cured leaf has 10,000 ppm nicotine and 100 ppb TSNA. A tobacco plant or portion thereof having a reduced amount of nicotine and/or TSNA, according to the invention, can have no detectable nicotine and/or TSNA, or may contain some detectable amounts of one or more TSNA and/or nicotine so long as the amount of nicotine and/or TSNA is less than that found in a control plant of the same variety. That is, a Burley tobacco leaf embodiment of the invention having a reduced amount of nicotine can have between 0 and 30,000 ppm nicotine and 0 and 8,000 ppb TSNA desirably between 0 and 20,000 ppm nicotine and 0 and 6,000 ppb TSNA more desirably between 0 and 10,000 ppm nicotine and 0 and 5,000 ppb TSNA preferably between 0 and 5,000 ppm nicotine and 0 and 4,000 ppb TSNA more preferably between 0 and 2,500 ppm nicotine and 0 and 2,000 ppb TSNA and most preferably between 0 and 1,000 ppm nicotine and 0 and 1,000 ppb TSNA. Embodiments of Burley leaf prepared by the methods described herein can also have between 0 and 1000 ppm nicotine and 0 and 500 ppb TSNA and some embodiments of Burley leaf prepared by the methods described herein have virtually no detectable amount of nicotine or TSNA.

Similarly, a Flue-cured tobacco leaf embodiment of the invention having a reduced amount of nicotine can have between 0 and 20,000 ppm nicotine and 0 and 300 ppb TSNA desirably between 0 and 15,000 ppm nicotine and 0 and 250 ppb TSNA more desirably between 0 and 10,000 ppm nicotine and 0 and 200 ppb TSNA preferably between 0 and 5,000 ppm nicotine and 0 and 150 ppb TSNA more preferably between 0 and 2,500 ppm nicotine and 0 and 100 ppb TSNA and most preferably between 0 and 1,000 ppm nicotine and 0 and 50 ppb TSNA. Embodiments of flue-cured tobacco prepared by the methods described herein can also have between 0 and 500 ppm nicotine and 0 and 25 ppb TSNA and some embodiments of flue-cured tobacco prepared by the methods described herein have virtually no detectable amount of nicotine or TSNA.

Further, an Oriental cured tobacco embodiment of the invention having a reduced amount of nicotine can have between 0 and 10,000 ppm nicotine and 0 and 100 ppb TSNA desirably between 0 and 7,000 ppm nicotine and 0 and 75 ppb TSNA more desirably between 0 and 5,000 ppm nicotine and 0 and 50 ppb TSNA preferably between 0 and 3,000 ppm nicotine and 0 and 25 ppb TSNA more preferably between 0 and 1,500 ppm nicotine and 0 and 10 ppb TSNA and most preferably between 0 and 500 ppm nicotine and no TSNA. Embodiments of Oriental cured tobacco prepared by the methods described herein can also have between 0 and 250 ppm nicotine and no TSNA and some embodiments of Oriental cured tobacco prepared by the methods described herein have virtually no detectable amount of nicotine or TSNA.

The present invention provides methods and nucleic acid constructs for producing such transgenic plants, as well as such transgenic plants. Such methods include the development of transgenic cassettes that will reduce (or eliminate) nicotine biosynthesis. Tobacco plants are transformed with an excess number of DNA sequences (cis-acting elements) from the promoters of genes encoding, but not limited to, QPTase and PMTase that are regulated in nicotine biosynthesis. These cis-acting elements are preferably integrated into the plant genome so as to allow for transfer to successive generations. Typically, the Nic1 and Nic2 DNA-binding proteins that interact with these cis-acting DNA sequences are expressed at relatively low levels in the cell, thus the excess of transgenic cis-acting elements will compete with the endogenous elements associated with the genes encoding, but not limited to. QPTase and PMTase for available Nic1 and Nic2. Accordingly, these cis-acting DNA sequences (and those of other cis-acting elements) are referred to herein as "decoys" or "molecular decoys". The competition decreases occupancy of trans-acting DNA-binding proteins on their cognate cis-acting elements, thereby down-regulating the synthesis of nicotine biosynthesis enzymes.

The present invention also provides DNA molecules of cis-acting elements of QPTase or PMTase, and vectors comprising those DNA molecules, as well as transgenic plant cells and plants transformed with those DNA molecules and vectors. Transgenic tobacco cells and plants of this invention are characterized by lower nicotine content than untransformed control tobacco cells and plants.

Tobacco plants with low levels of nicotine production, or substantially no nicotine production, are attractive as recipients for transgenes expressing commercially valuable products such as pharmaceuticals, cosmetic components, or food additives. Tobacco is attractive as a recipient plant for a transgene encoding a desirable product, as tobacco is easily genetically engineered and produces a very large biomass per acre; tobacco plants with reduced resources devoted to nicotine production accordingly will have more resources available for production of transgene products. Methods of transforming tobacco with transgenes producing desired products are known in the art; any suitable technique may be utilized with the low nicotine tobacco plants of the present invention.

Tobacco plants according to the present invention with reduced QPTase and PMTase expression and reduced nicotine levels will be desirable in the production of tobacco products having reduced nicotine and/or TSNA content. The tobacco plants described herein are suitable for conventional growing and harvesting techniques (e.g. topping or no topping, bagging the flowers or not bagging the flowers, cultivation in manure rich soil or without manure) and the harvested leaves and stems are suitable for use in any traditional tobacco product including, but not limited to, pipe, cigar and cigarette tobacco, and chewing tobacco in any form including leaf tobacco, shredded tobacco, or cut tobacco.

It is also contemplated that the low nicotine and/or TSNA tobacco described herein can be processed and blended with conventional tobacco so as to create a wide-range of tobacco products with varying amounts of nicotine and/or nitrosamines. These blended tobacco products can be used in tobacco product cessation programs so as to slowly move a consumer from a high nicotine and TSNA product to a low nicotine and TSNA product. For example, a smoker can begin the program smoking blended cigarettes having 10 mg of nicotine and 1.5 mg of nitrosamine, gradually move to smoking cigarettes with 7 mg of nicotine and 1 mg of nitrosamine, followed by cigarettes having 5.0 mg nicotine and 0.5 mg nitrosamine, followed by cigarettes having 2.0 mg nicotine and 0.25 mg nitrosamine, followed by cigarettes having 1.0 mg nicotine and no TSNA until the consumer decides to smoke only the cigarettes having virtually no nicotine and nitrosamines or quitting smoking altogether. Accordingly, the blended cigarettes described herein provide the basis for an approach to reduce the carcinogenic potential in a human in a step-wise fashion.

1. Nucleic Acids Encoding Cis-acting Elements such as Nic Gene Product Responsive Elements.

Any of a variety of cis-acting elements can be used in carrying out the present invention, depending upon the particular application of the present invention. Examples of cis-acting elements (and corresponding transcription factors) that may be used, alone or in combination with one another, in practicing the present invention include, but are not limited to, AS-1 and ASF-1 (see U.S. Pat. Nos. 4,990,607 and 5,223,419), the AATT repeat element and PABF (see U.S. Pat. Nos. 5,834,236 and 6,191,258), a wounding-responsive cis-acting element from potato (Siebert et al., *Plant Cell* 1:961–8 (1989)), an embryo-specific cis-acting element from bean (Bustos et al, *Plant Cell* 1:839–853 (1989)), a root-specific cis-acting element from the tobacco RB7 promoter (U.S. Pat. No. 5,459,252 and Yamamoto et al., *Plant Cell* 3:371–382 (1991)), a positive poly(dA-dT) regulatory element and binding protein and negative CCCAA repeat element and binding protein (Wang et al., *Mol. Cell Biol.* 12:3399–3406 (1992)), a root-tip regulatory element from the tobacco phytochrome A1 promoter of tobacco (Adam et al., *Plant Mol Biol* 29:983–993 (1995)), an anaerobiosis-reponsive element from the maize glyceraldehyde-3-phosphate dehydrogenase 4 gene (Geffers et al., *Plant Mol Biol* 43:11–21 (2000)), and a seed-specific regulatory region from an *Arabidopis oleosin* gene (see U.S. Pat. No. 5,792,922), all of which are hereby expressly incorporated by reference in their entireties.

The status of the art is such that large databases list identified cis-acting regulatory regions (e.g., Plant Cis-acting Regulatory elements, "PLACE", with some 1,340 entries, see http://www.dna.affrc.gojp/hotdocs/PLACE/, and Plant Cis-acting Regulatory Elements "PlantCARE", which lists some 159 plant promoter, see http:// sphinx.rug.ac.be:8080/PlantCARE/. The listed cis-acting regulatory elements in these databases and the cis-acting regulatory elements that are provided in Raumbauts et al., Nucleic acids Research 27:295–296 (1999), and Higo et al., Nucleic acids Research 27:297–300 (1999) can be used with embodiments of the invention. Accordingly, the databases and references above are hereby expressly incorporated by reference in their entireties. Additional examples of cis-acting regulatory regions, which can be used with embodiments of the invention include: Lacombe E, Van Doorsselaere J, Boerjan W, Boudet A M, Grima-Pettenati J, Characterization of cis-elements required for vascular expression of the cinnamoyl CoA reductase gene and for protein-DNA complex formation Plant J 23: 663–676 (2000); Tilly J J, Allen D W, Jack T The CArG boxes in the promoter of the Arabidopsis floral organ identity gene APETALA3 mediate diverse regulatory effects Development 125: 1647–1657 (1998); Cordes S., Deikman J., Margossian L. J., Fischer R. L. Interaction of a developmentally regulated DNA-binding factor with sites flanking two different fruit-ripening genes from tomato Plant Cell 1(10):1025–1034 (1989); Hagen G., Martin G., Li Y., Guilfoyle T. Auxin-induced expression of the soybean GH3 promoter in transgenic tobacco plants" Plant Mol. Biol. 17:567–569 (1991); Pastuglia M., Roby D., Dumas C., Cock J. M., Rapid induction by wounding and bacterial infection of an S gene family receptor-like kinase in Brassica oleracea, Plant Cell 9:1–13 (1997); Grierson C, Du J S, Zabala M T, Beggs K, Smith C, Holdsworth M, Bevan M Separate cis sequences and trans factors direct metabolic and developmental regulation of a potato tuber storage protein gene Plant J 5:815–826 (1994); MBSI, Petunia hybrida MYB binding site involved in flavonoid biosynthetic gene regulation, Koes R. E., Spelt C. E., van Den Elzen P. J. M., Mol J. N. M. Cloning and molecular characterization of the chalcone synthase multigene family of Petunia hybrida, Gene 81:245–257 (1989); Inaba T., Nagano Y., Sakakibara T., Sasaki Y., Identification of a cis-regulatory element involved in phytochrome down-regulated expression of the pea small GTPase gene pra2, Plant Physiol. 120:491–499(1999); DRE, Arabidopsis thaliana cis-acting element involved in dehydration, low-temperature, salt stresses, Yamaguchi-Shinozaki K., Shinozaki K., Arabidopsis DNA encoding two desiccation-responsive rd29 genes, Plant Physiol. 101:1119–1120 (1993); Rushton P. J., Torres J. T., Parniske M., Wernert P., Hahlbrock K., Somssich I. E., Interaction of elicitor-induced DNA-binding proteins with elicitor response elements in the promoters of parsley PR1 genes, EMBO J. 15(20):5690–5700 (1996); MSA-like cis-acting element involved in cell cycle regulation, Ito M., Criqui M. C., Sakabe M., Ohno T., Hata S., Kouchi H., Hashimoto J, Fukuda H., Komamine A., Watanabe A. Cell-cycle regulated transcription of A- and B-type plant cyclin genes in synchronous cultures, Plant J. 11:983–992 (1997), all of which are hereby expressly incorporated by reference in their entireties. In general, preferred are elements that are not critical to sustaining life of the host cell (e.g., not associated with "housekeeping genes" that are essential for basic cell functions), but are functionally associated with regulating transcription of a gene or family of genes that result in a non-lethal phenotypic change in the plant.

Nic gene product responsive elements can be isolated by screening the promoter region of genes that are transcriptionally activated by the Nic gene product in the same manner as described herein, or can be identified by hybridization to SEQ ID NO: 1 herein and subsequent screening for the ability to bind the Nic gene product in the manner described below.

Nucleic acid sequences employed in carrying out the present invention include naturally occurring or synthetic fragments with sequence similarity to SEQ ID NO:1 or a fragment thereof consisting of, desirably, at least 20–455 consecutive nucleotides, preferably, at least 30–400 consecutive nucleotides, more preferably, 50–350 consecutive nucleotides, and, most preferably, 100–300 or 200–400 consecutive nucleotides. This definition is intended to encompass natural allelic variations of DNA of SEQ ID NO:1 or said fragments. Thus, DNA sequences that hybridize to DNA of SEQ ID NO:1, or the complement thereof, may also be employed in carrying out the present invention. Preferred embodiments include fragments of SEQ ID NO:1, or other Nic gene product responsive elements (i.e., elements that bind to the complement of SEQ ID NO:1), that retain the ability to bind the Nic gene product. Such fragments will, in general, be continuous fragments or portions of the naturally occurring construct that are at least 20, 40 or 60 nucleotides in length. Conditions which permit other DNA sequences with sequence similarity to SEQ ID NO:1 can be determined in a routine manner. For example, hybridization of such sequences may be carried out under conditions of reduced stringency or even stringent conditions (e.g., conditions represented by a wash stringency of 0.3 M NaCl, 0.03 M sodium citrate, 0.1% SDS at 60° C. or even 70° C. to DNA with the sequence given herein as SEQ ID NO:1 using a standard in situ hybridization assay. See J. Sambrook et al., Molecular Cloning, A Laboratory Manual (2d Ed. 1989)(Cold Spring Harbor Laboratory)). In general, such sequences will be at least 65% similar, 75% similar, 80% similar, 85% similar, 90% similar, or even 95% similar, or more, with the sequence given herein as SEQ ID NO:1. Determinations of sequence similarity are made with the two sequences aligned for maximum matching; gaps in either of the two sequences being matched are allowed in maximizing matching. Gap lengths of 10 or less are preferred, gap lengths of 5 or less are more preferred, and gap lengths of 2 or less still more preferred.

The DNA sequence of the present invention may consist essentially of the sequence provided herein (SEQ ID NO:1), or equivalent nucleotide sequences representing alleles or polymorphic variants of these genes, or coding regions thereof.

Use of the phrase "substantial sequence similarity" in the present specification and claims means that DNA, RNA or amino acid sequences which have slight and non-consequential sequence variations from the actual sequences disclosed and claimed herein are considered to be equivalent to the sequences of the present invention. In this regard, "slight and non-consequential sequence variations" mean that "similar" sequences (i.e., the sequences that have substantial sequence similarity with the DNA, RNA, or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

Additional nucleic acid sequence for use with aspects of the invention include the Nic gene product responsive element, which can be obtained from the sequence disclosed in U.S. Pat. No. 5,459,252, herein expressly incorporated by reference in its entirety. In some embodiments, the Nic gene product responsive element resides between −1000 and −600 or −700 bp of the NtQPT1 promoter. Accordingly, some embodiments involve a 300–400 nucleotide long fragment of the NtQPT1 promoter that corresponds to the sequence of the NtQPT1 promoter between −1000 and −600 or −700, as disclosed in U.S. Pat. No. 5,459,252.

DNA sequences provided herein can be transformed into a variety of host cells, as discussed below. A variety of suitable host cells, having desirable growth and handling properties, are readily available in the art.

Use of the phrase "isolated" or "substantially pure" in the present specification and claims as a modifier of DNA, RNA, polypeptides or proteins means that the DNA, RNA, polypeptides or proteins so designated have been separated from their in vivo cellular environments through the efforts of human beings. As used herein, a "native DNA sequence" or "natural DNA sequence" means a DNA sequence which can be isolated from non-transgenic cells or tissue. Native DNA sequences are those which have not been artificially altered, such as by site-directed mutagenesis. Once native DNA sequences are identified, DNA molecules having native DNA sequences may be chemically synthesized or produced using recombinant DNA procedures as are known in the art. As used herein, a native plant DNA sequence is that which can be isolated from non-transgenic plant cells or tissue. As used herein, a native tobacco DNA sequence is that which can be isolated from non-transgenic tobacco cells or tissue 2. Nucleic Acid Constructs and Transfer Vectors.

Nucleic acid constructs, or "cassettes," of the present invention include a cis-acting element such as a Nic gene product responsive element as described above, typically as a recombinant construct in a linear or circular nucleic acid that serves as a transfer vector for introducing the Nic gene product into plant cells.

The construct or cassette may be provided in a DNA construct which also has at least one replication system. For convenience, it is common to have a replication system functional in *Escherichia coli* such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host-range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in an eukaryotic host, particularly the plant host. The markers may be protection against a biocide, such as antibiotics, toxins, heavy metals, or the like; may provide complementation, by imparting prototrophy to an auxotrophic host; or may provide a visible phenotype through the production of a novel compound in the plant.

Nucleic acid constructs of the present invention may include one or more matrix attachment regions positioned 5', 3', or both 5' and 3' to the cis-acting element(s) to enhance the stability and/or hereditability thereof, as described in U.S. Pat. No. 5,773,689 to Thompson et al., U.S. Pat. No. 5,773,695 to Thompson et al., U.S. Pat. No. 6,245,974 to Michalowski et al., U.S. Pat. No. 6,239,328 to Thompson et al., U.S. Pat. No. 6,100,448 to Thompson et al., and U.S. Pat. No. 6,037,525 to Thompson et al., the disclosures of which are incorporated by reference herein in their entirety.

The various fragments comprising the various constructs, cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature as exemplified by J. Sambrook et al., Molecular Cloning, A Laboratory Manual (2d Ed. 1989)(Cold Spring Harbor Laboratory).

Vectors which may be used to transform plant tissue with nucleic acid constructs of the present invention include both ballistic vectors and *Agrobacterium* vectors, as well as vectors suitable for DNA-mediated transformation. These are discussed in greater detail below.

The nucleic acid constructs molecules and vectors used to produce the transformed cells and plants of this invention may further comprise a dominant selectable marker gene. Suitable dominant selectable markers for use in tobacco include, inter alia, antibiotic resistance genes encoding neomycin phosphotransferase (NPTII), hygromycin phosphotransferase (HPT), and chloramphenicol acetyltransferase (CAT). Another well-known dominant selectable marker suitable for use in tobacco is a mutant dihydrofolate reductase gene that encodes methotrexate-resistant dihydrofolate reductase. DNA vectors containing suitable antibiotic resistance genes, and the corresponding antibiotics, are commercially available.

3. Plant Transformation, Regeneration and Propagation.

Transformed cells are selected out of the surrounding population of non-transformed cells by placing the mixed population of cells into a culture medium containing an appropriate concentration of the antibiotic (or other compound normally toxic to the cells) against which the chosen dominant selectable marker gene product confers resistance. Thus, only those plant cells that have been transformed will survive and multiply.

Methods of making recombinant plants of the present invention, in general, involve first providing a plant cell capable of regeneration (the plant cell typically residing in a tissue capable of regeneration). The plant cell is then transformed with a DNA construct comprising a cassette of the present invention (as described herein) and a recombinant plant is regenerated from the transformed plant cell. As explained below, the transforming step is carried out by techniques as are known in the art, including but not limited to bombarding the plant cell with microparticles carrying the transcription cassette, infecting the cell with an *Agrobacterium tumefaciens* containing a Ti plasmid carrying the cassette, or any other technique suitable for the production of a transgenic plant.

Microparticles carrying a DNA construct of the present invention, which microparticle is suitable for the ballistic transformation of a plant cell, are also useful for making transformed plants of the present invention. The microparticle is propelled into a plant cell to produce a transformed plant cell, and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Christou et al., U.S. Pat. No. 5,015,580 (the disclosures of all U.S. Patent References cited herein are to be incorporated herein by reference). When using ballistic transformation procedures, the cassette may be incorporated into a plasmid capable of replicating in or integrating into the cell to be transformed. Examples of microparticles suitable for use in such systems include 1 to 5 micrometer ($\mu$m) gold spheres. The DNA construct may be deposited on the microparticle by any suitable technique, such as by precipitation.

Numerous *Agrobacterium* vector systems useful in carrying out the present invention are known. For example, U.S. Pat. No. 4,459,355 discloses a method for transforming susceptible plants, including dicots, with an *Agrobacterium* strain containing the Ti plasmid. The transformation of woody plants with an *Agrobacterium* vector is disclosed in U.S. Pat. No. 4,795,855. Further, U.S. Pat. No. 4,940,838 to Schilperoort et al. discloses a binary *Agrobacterium* vector (i.e., one in which the *Agrobacterium* contains one plasmid having the vir region of a Ti plasmid but no T region, and a second plasmid having a T region but no vir region) useful in carrying out the present invention.

As a high copy number of decoy sequences must typically be present in the genome, tandem copies of the cis-acting element(s) could be inserted into an *Agrobacterium* vector, but the preferred method of plant transformation is by particle bombardment which introduces multiple copies of the transgenic DNA into the plant genome. The actual number of the cis-acting element (whether each individually present on a vector such as a plasmid, counting multiple copies on a single vector or plasmid, or combinations thereof) that must be inserted into the host cells (and progeny or daughter cells thereof) to obtain increased or decreased levels of the protein of interest in the cells and plants of the invention will depend in part upon the particular element, but in general will be at least 20, 30 or 50 to about 500, 1,000 or 2,000, or more.

Plant species may be transformed with the DNA construct of the present invention by the DNA-mediated transformation of plant cell protoplasts and subsequent regeneration of the plant from the transformed protoplasts in accordance with procedures well known in the art. Fusion of tobacco protoplasts with DNA-containing liposomes or via electroporation is known in the art. (Shillito et al., "Direct Gene Transfer to Protoplasts of Dicotyledonous and Monocotyledonous Plants by a Number of Methods, Including Electroporation", *Methods in Enzymology* 153, 313–36 (1987)).

As used herein, "transformation" refers to the introduction of exogenous DNA into cells, so as to produce transgenic cells stably transformed with the exogenous DNA. By "stably transformed" is meant that the exogeneous nucleic acid is passed to daughter or progeny cells of the initially transformed cells, and preferably passed to or inherited by progeny plants of the transformed plants (including sexually and asexually reproduced progeny plants).

Transformed cells are induced to regenerate intact plants through application of cell and tissue culture techniques that are well known in the art. The method of plant regeneration is chosen so as to be compatible with the method of transformation. After regeneration of transgenic plants from transformed cells, the introduced DNA sequence is readily transferred to other plant varieties through conventional plant breeding practices and without undue experimentation.

For example, to analyze the segregation of the transgenic DNA, regenerated transformed plants ($R_0$) may be grown to maturity, tested for levels of the protein of interest, and selfed to produce $R_1$ plants. A percentage of $R_1$ plants carrying the transgenic DNA are homozygous for the transgenic DNA. To identify homozygous $R_1$ plants, transgenic $R_1$ plants are grown to maturity and selfed. Homozygous $R_1$ plants will produce $R_2$ progeny where each progeny plant carries the transgenic DNA; progeny of heterozygous $R_1$ plants will segregate 3:1.

Nicotine serves as a natural pesticide which helps protect tobacco plants from damage by pests. It may therefore be desirable to additionally transform low or no nicotine plants produced by the present methods with a transgene (such as *Bacillus thuringiensis*) that will confer additional insect protection.

A preferred plant for use in the present invention is any species of the genus *Nicotiana*, or tobacco, including *N. tabacum, N. rustica* and *N. glutinosa*. Any strain or variety of tobacco may be used.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, callus tissue, existing meristematic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the cassette); the plants may comprise grafts of transformed and untransformed tissues (e.g., a transformed root stock grafted to an untransformed scion in *citrus* species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt11) can be associated with the construct to assist in breeding.

In some preferred embodiments of the invention, to help insure that a sufficient number of decoy or cis-acting elements are inserted in cells and retained over many cell divisions to produce a transgenic plant with altered levels of protein or proteins therein, biolistic transformation is used as described above, circular DNA or plasmids are used to carry the cis-acting decoy segments as described above, the circular DNA or plasmids that are used are relatively small (e.g., they consist of less than 10,000 or less than 6,000 base pairs), and a high molar ratio of the cis-acting element to selectable marker (e.g., 10 to 1) is inserted into the host cells.

As used herein, a crop comprises a plurality of plants of the present invention, and of the same genus, planted together in an agricultural field. By "agricultural field" is meant a common plot of soil or a greenhouse. Thus, the present invention provides a method of producing a crop of plants having altered levels of a protein of interest, (e.g., QPTase and PMTase activity and thus having decreased nicotine levels), compared to a similar crop of non-transformed plants of the same species and variety.

While the invention describes methods to reduce nicotine levels in transgenic tobacco, this method can also be employed to phenocopy mutations in trans-acting transcriptional activators and repressors without cloning their respective genomic loci. Promoter regions of a gene can be analyzed, using technology known by those skilled in the art, to define regions of the promoter that respond to transcription factors. Typically, this is done by deletion analysis of the promoter. Nested deletions of the promoter are fused to a reporter gene and expression of the reporter gene is monitored in transgenic organisms. Isolation of transcription factors using current technologies is very difficult; the present invention circumvents the necessity of cloning the cognate transcription factors for applications in which it is desirable to disrupt any set of genes that are coordinately regulated by one or more transcriptional activators. Conversely, the process would up-regulate the expression of any set of genes that are coordinately regulated by one or more transcriptional repressor.

As noted above, the present invention could be employed to disrupt gene expression and down-regulate the expression of a protein of interest that is under the control of a cis-acting activating element in a variety of host cells, including plant (particularly vascular plant such as monocot and dicot), animal (avian, mammalian), fungi, or bacteria cells, both in vivo and in vitro. In bacteria and fungi, multicopy plasmids can be used to increase copies of molecular decoy present in the cell.

The examples which follow are set forth to illustrate the present invention, and are not to be construed as limiting thereof.

EXAMPLE 1

Localization of Cis-acting Element in NtOPT1 Promoter

Figure 2:
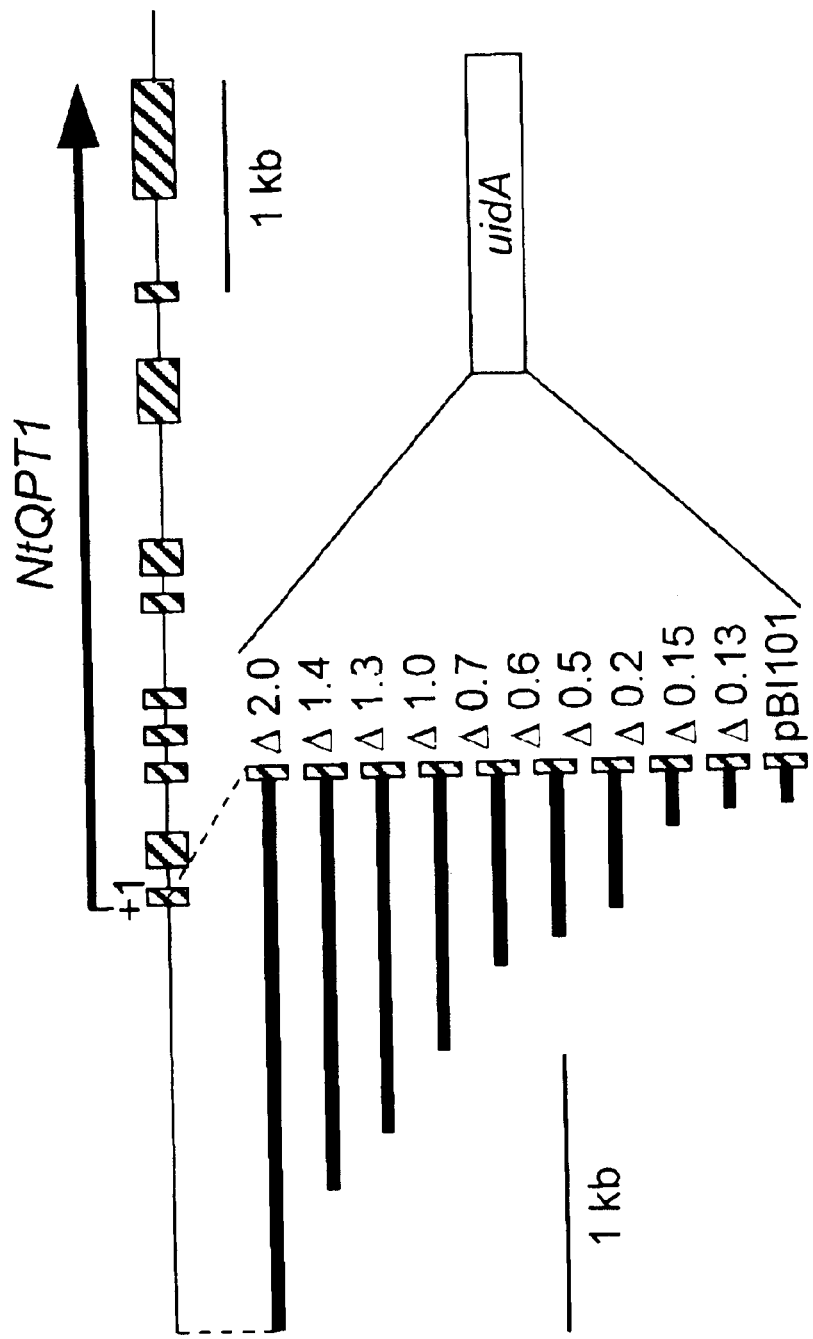
FIG. 2 shows a diagrammatic representation of the NtQPT1 gene and the NtQPT1 promoter-uidA chimeras. The site of transcription initiation is indicated (+1) and the arrow indicates the NtQPT1 transcript. Ten exons are presented as crosshatched bars. The deletion series of the promoter is also shown as solid bars truncated from the 5' end of the promoter. Sizes of promoter fragments fused to the uidA gene, which encodes β-glucuronidase (GUS) are indicated (i.e. Δ2.0, Δ1.4, etc.) in kilobase pairs (kb). Chimeric NtQPT1 promoter-uidA fusions were cloned into pBI101.

To characterize the minimal sequence required for the NtQPT1 cis-acting element, the promoter region of the NtQPT1 gene was isolated, truncated at the 5' end, and fused to the gene encoding β-glucuronidase (GUS) to assess function as a specific enhancer of nicotine production. The NtQPT1 gene was isolated and sequenced. The start of the transcript was determined by comparing the TobRD2 cDNA sequence to the genomic locus sequence. Sequence located 5' of the transcription start site was defined as promoter sequence. Using PCR primers and the promoter as a template, truncations were made at the 5' end of the promoter to determine minimal cis-acting enhancer sequence (see FIG. 2). The truncations were fused to the uidA gene, which encodes GUS. The fusion gene was inserted into a vector and transformed by standard methods of ballistic transformation into *Nicotiana tabacum* Burley 21.

Figure 3:
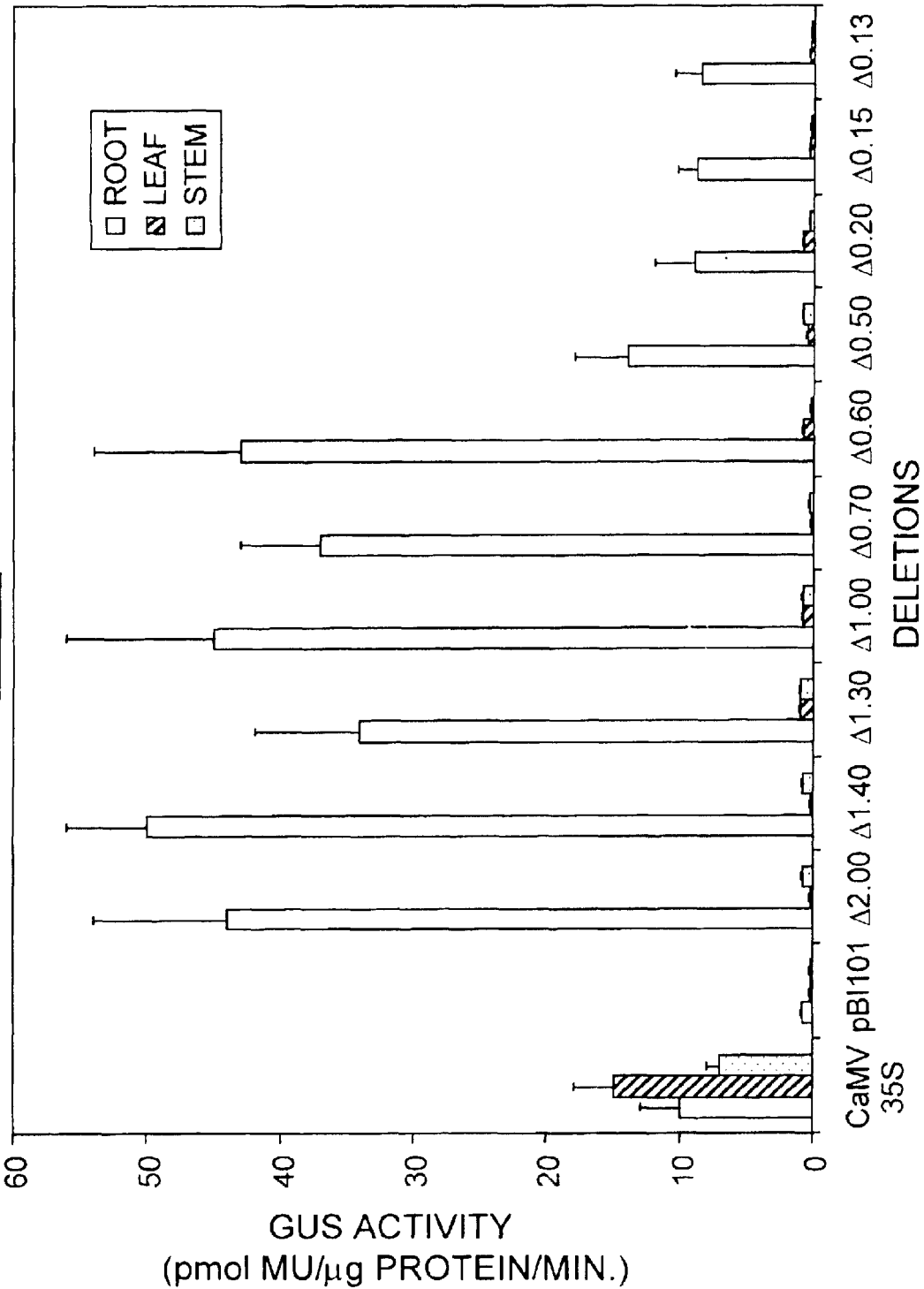
FIG. 3 shows β-glucuronidase (GUS) activity in roots, leaves, and stems of transgenic tobacco plants carrying the CaMV 35S promoter (CaMV 35S), the promoterless GUS (pBI101), and 5' nested deletions of the TobRD2 (gene encoding NtQPT1) promoter fused to GUS. Sizes of promoter fragments fused to the uidA gene are indicated (i.e. Δ2.0, Δ1.4, etc.) in kilobase pairs (kb). For each construct at least 20 independent transformants were assayed.

GUS activity was assessed by dividing plants into roots, stems, and leaves. Each plant tissue, transformed with a different NtQPT1 truncation construct, was ground with a morter and pestle, proteins were extracted with NaPO$_4$ buffer, pH 7.0, X-Glc (100 ug/mL) was added, and the assay was carried out at 37° C. for 30 min. GUS activity was measured at 595 nm). For each construct at least 20 independent transformants were assayed. A mean and standard deviation was determined. GUS activity in truncations was compared to a CaMV 35S-GUS fusion and a promoterless GUS(pBI101) control. Maximal GUS activity, representing NtQPT1 expression, was obtained when −586 to −2000 bp was fused to the uidA gene (FIG. 3). Shorter promoters from −1 to −586 did not support high levels of uidA expression. Therefore, the NtQPT1 cis-acting element is located between −586 and −2000 bp 5' of the transcription start site.

EXAMPLE 2

Localization of Nic Gene Product Binding Site in NtOPT1 Promoter

The NtQPT1 promoter deletion series fused to the uida reporter gene (encoding GUS) was transformed into nic$^-$/nic$^-$ homozygous *N. tabacum* plants. R$_0$ transformants having the transgenic DNA at a single locus were crossed with nic$^-$/nic$^-$ or Nic$^+$/Nic$^+$ homozygous plants to give homozygous (nic$^-$/nic$^-$) and heterozygous (Nic$^+$/nic$^-$) progeny carrying the transgene (NtQPT1 promoter-GUS) at the same chromosomal location. GUS activity was quantified in multiple progeny from multiple, independent transformants and compared between Nic$^+$ and nic$^-$ phenotypes (TABLE 1). Ratios greater than 1.5 were determined to contain the cis-acting elements responding to Nic gene product activation.

TABLE 1

Regulation of NtQPT1 Promoter-Directed GUS Expression by the Nic Gene Products in Tobacco.

| Promoter | Independent Transformants | GUS activity in Nic$^+$/nic$^{-2}$ | GUS activity in nic$^-$/nic$^{-2}$ | GUS ratio of Nic/nic |
|---|---|---|---|---|
| 2.0 (2010)[1] | 2 | 111.7 (7) | 21.2 (5) | 5.3 |
|  |  | 46.6 (6) | 11.9 (8) | 5.6 |
| 1.3 (1306)[1] | 2 | 92.4 (6) | 16.6 (4) | 5.5 |
|  |  | 93.9 (7) | 12.9 (5) | 7.3 |
| 1.0 (1042)[1] | 3 | 55.7 (6) | 18.3 (4) | 3.0 |
|  |  | 74.1 (6) | 27.5 (7) | 2.7 |
|  |  | 78.0 (5) | 17.2 (7) | 4.5 |
| 734 | 1 | 5.5 (5) | 3.5 (5) | 1.5 |
| 586 | 3 | 47.55 (5) | 44.9 (5) | 1.06 |
|  |  | 24.3 (3) | 16.0 (36) | 1.5 |
|  |  | 29.1 (33) | 30.3 (19) | 0.97 |
| 535 | 3 | 71.6 (10) | 50.3 (5) | 1.4 |
|  |  | 54.0 (5) | 40.7 (3) | 1.3 |
|  |  | 51.9 (5) | 67.8 (5) | 0.8 |
| CaMV 35S | 4 | 32.7 (4) | 19.6 (4) | 1.7 |
|  |  | 44.8 (6) | 47.6 (3) | 0.94 |
|  |  | 54.8 (5) | 40.6 (5) | 1.3 |
|  |  | 9.7 (4) | 8.6 (3) | 1.1 |

GUS activity is expressed as pmol MU/μg protein/min.
[1]Actual promoter size (bp) is indicated in parenthesis.
[2]Number in parenthesis indicates the number of plants tested.

These experiments demonstrated that binding of Nic gene products is located between approximately −1000 and −600 or −700 bp of the NtQPT1 promoter as determined by GUS activity in Nic$^+$/nic$^-$ and nic$^-$/nic$^-$ plants.

EXAMPLE 3

Regulation of NtQPT1 Gene Expression Using Molecular Decoys

Nucleotide sequence located between −1000 and −600 or −700 bp of the NtQPT1 promoter is inserted in tandem arrays into a plant-*Agrobacterium* shuttle vector and subsequently transformed into tobacco via methods known to one skilled in the art. Plants stably transformed with said vector are assessed for the level of expression of NtQPT1 and for nicotine and/or TSNA content. These experiments will demonstrate that tobacco transformed with molecular decoys that interact with Nic gene products will exhibit a reduced amount of nicotine and/or TSNA. Plants with multiple tandem insertions of the molecular decoy which have reduced NtQPT1 expression and reduced nicotine levels are used for expression of commercially valuable products and production of tobacco products having reduced nicotine and/or TSNA content.

EXAMPLE 4

Regulation of ASF-1 Binding Using a TGACG Molecular Decoy

The nucleotide sequence TGACG is inserted in tandem arrays into a plant-*Agrobacterium* shuttle vector and transformed into a plant such as pea via methods known to one skilled in the art. Plants stably transformed with said vector have reduced binding activity of trans-acting DNA binding factor ASF-1 which recognizes the sequence motif TGACG which is found in plant genes such as histone genes (Mikami et al., (1987) FEBS Lett. 223:273); enzyme genes for agropine biosynthesis (Velten et al., EMBO J. 3:2723–30); the octopine synthase gene (Ellis et al., EMBO J. 6:3203); and the mannopine synthase gene (DeRita and Gelvin, (1987) Mol. Gen. Genet. 207:233); as well as the CaMV35S gene, histone H3 gene and nopaline synthase gene.

EXAMPLE 5

Regulation of Spatial and Temporal Expression of Beta-Phaseolin Using Molecular Decoys The nucleotide sequence corresponding to UAS1 (−295 to −109) of the beta-phaseolin gene is inserted in tandem arrays into a plant-*Agrobacterium* shuttle vector and transformed into a bean plant via methods known to one skilled in the art. Plants stably transformed with said vector have reduced binding activity of trans-acting DNA binding factor PvALF which recognizes the sequences CATGCAAA and CATG-CATG located in UAS1 (Bobb et al. (1997) *Nucleic Acids Res* 25(3):641–7). Plants with reduced binding of PvALF would have reduced expression of seed-specific expression of beta-phaseolin primarily in cotyledons and shoot meristem (Bustos et al. (1991) *EMBO J.* 10(6):1469–1479).

Transformation of tandem arrays of nucleotide sequences corresponding to the vicilin-box (GCCACCTCAA; SEQ ID NO:2) and site B (CACACGTCAA; SEQ ID NO:3) of the beta-phaseolin gene into a bean plant results in the reduced binding activity of trans-acting DNA binding factors ROM1 and ROM2 leading to premature onset of beta-phaseolin expression. ROM1 and ROM2 proteins function as repressors of beta-phaseolin and phytohemagglutinin L-subunit expression to block onset of seed maturation (U.S. Pat. No. 6,160,202 to Bustos; Chem et al. (1996) *Plant Cell* 8:305–321; Chem et al. (1996) *Plant J.* 10:135–148).

EXAMPLE 6

Regulation of Plant Gene Expression Using Molecular Decoys

Transformation of tobacco plants with tandem arrays of the root-specific cis-acting element from the tobacco RB7 promoter (U.S. Pat. No. 5,459,252 to Conkling et al.; Yamamoto et al. (1991) *Plant Cell* 12:3399–3406), which codes for a structural gene, results in the reduced binding activity of the trans-acting DNA binding factor of the RB7 cis-acting element.

Likewise, similar tandem arrays of the following cis-elements are transformed into the plants to reduce binding activity of the corresponding trans-acting DNA binding factors: the AATT cis-acting repeat element and its corresponding PABF trans-acting factor (see U.S. Pat. Nos. 5,834,236 and 6,191,258); the positive poly(dA-dT) regulatory element and binding protein and negative CCAA repeat element and binding protein (Wang et al. (1992) *Mol. Cell Biol.* 12:3399–3406); the root-tip regulatory element from the tobacco phytochrome A1 promoter of tobacco (Adam et al. (1995) *Plant Mol. Biol.* 29:983–993); the anaerobiosis-responsive element from the maize glyceraldehyde-3-phosphate dehydrogenase 4 gene (Geffers et al. (2000) *Plant Mol. Biol.* 43:11–21); and the seed-specific regulatory region from an *Arabidopsis oleosin* gene (see U.S. Pat. No. 5,792,922).

EXAMPLE 7

Tobacco Having Reduced Nicotine and/or TSNA Levels Generated Using Molecular Decoys Multiple copies of an approximately 300 or 400 nucleotide long fragment of the NtQPT1 promoter (e.g., including nucleotide sequence located between −1000 and −600 or −700 bp of the NtQPT1 promoter, such as SEQ ID NO:1) are affixed to microparticles (e.g., by precipitation) that are suitable for the ballistic transformation of a plant cell (e.g., 1 to 5 $\mu$m gold spheres). The microparticles are propelled into tobacco plant cells (e.g., Burley 21 LA) so as to produce transformed plant cells, and plants are regenerated from the transformed plant cells. Burley 21 LA is a variety of Burley 21 with substantially reduced levels of nicotine as compared with Burley 21 (i.e., Burley 21 LA has 8% the nicotine levels of Burley 21, see Legg et al., *Can J Genet Cytol*, 13:287–91 (1971); Legg et al., *J Hered*, 60:213–17 (1969))

Any suitable ballistic cell transformation methodology and apparatus can be used. Exemplary apparatus and procedures are disclosed in Sanford and Wolf, U.S. Pat. No. 4,945,050, and in Christou et al., U.S. Pat. No. 5,015,580, both of which are herein expressly incorporated by reference in their entireties. Optionally, the transformed nucleic acid can include a gene encoding a selectable marker (e.g., a marker that allows for positive or negative selection of transformants) or the molecular decoys can be co-transferred with a selectable marker gene. In this manner, positive transformants can be easily identified.

Transformed cells, tissues, and seedlings are grown on Murashige-Skoog (MS) medium (with or without the selection compound, e.g., antibiotic, depending on whether a selectable marker was used. One-hundred independent transformants of Burley 21 LA ($T_0$) are allowed to self. Progeny of the selfed plants ($T_1$) are germinated. Nicotine levels of $T_1$ progeny are measured qualitatively using a micro-assay technique. Approximately ~200 mg fresh tobacco leaves are collected and ground in 1 ml extraction solution. (Extraction solution: 1 ml Acetic acid in 100 ml $H_2O$) Homogenate is centrifuged for 5 min at 14,000×g and supernatant removed to a clean tube, to which the following reagents are added: 100 $\mu$L $NH_4OAC$ (5 g/100 ml $H_2O$+50 $\mu$L Brij 35); 500 $\mu$L Cyanogen Bromide (Sigma C-6388, 0.5 g/100 ml $H_2O$+50 $\mu$L Brij 35); 400 $\mu$L Aniline (0.3 ml buffered Aniline in 100 ml $NH_4OAC$ +50 $\mu$L Brij 35). A nicotine standard stock solution of 10 mg/ml in extraction solution is prepared and diluted to create a standard series for calibration. Absorbance at 460 nm is read and nicotine content of test samples are determined using the standard calibration curve.

$T_1$ progeny that have less than 10% of the nicotine levels of the Burley 21 LA parent are allowed to self to produce $T_2$ progeny. Homozygous $T_2$ progeny are then identified. Nicotine levels in homozygous and heterozygous $T_2$ progeny are also qualitatively determined using the micro-assay. Leaf samples of homozygous $T_2$ progeny can also be sent to the Southern Research and Testing Laboratory in Wilson, NC for quantitative analysis of nicotine levels using Gas Chromatography/Flame Ionization Detection (GC/FID). Homozygous $T_2$ progeny of will have nicotine levels that are substantially reduced as compared to the untransformed tobacco (e.g., ~70 ppm). Because the nicotine levels in such plants are substantially reduced, the TSNA levels in these plants is concomitantly reduced.

These experiments will demonstrate that tobacco transformed with molecular decoys that interact with Nic gene products will exhibit a reduced amount of nicotine and/or TSNA. Plants with multiple tandem insertions of the molecular decoy which have reduced NtQPT1 expression and reduced nicotine levels are used for expression of commercially valuable products and production of tobacco products having reduced nicotine and/or TSNA content.

EXAMPLE 8

Low Nicotine and TSNA Blended Tobacco

The following example describes several ways to create tobacco products having specific amounts of nicotine and/or TSNAs through blending. Some blending approaches begin with tobacco prepared from varieties that have extremely low amounts of nicotine and/or TSNAs. By blending prepared tobacco from a low nicotine/TSNA variety (e.g., undetectable levels of nicotine and/or TSNAs) with a conventional tobacco (e.g., Burley, which has 30,000 parts per million (ppm) nicotine and 8,000 parts per billion (ppb) TSNA; Flue-Cured, which has 20,000 ppm nicotine and 300 ppb TSNA; and Oriental, which has 10,000 ppm nicotine and 100 ppb TSNA), tobacco products having virtually any desired amount of nicotine and/or TSNAs can be manufactured. Tobacco products having various amounts of nicotine and/or TSNAs can be incorporated into tobacco use cessation kits and programs to help tobacco users reduce or eliminate their dependence on nicotine and reduce the carcinogenic potential.

For example, a step 1 tobacco product can be comprised of approximately 25% low nicotine/TSNA tobacco and 75% conventional tobacco; a step 2 tobacco product can be comprised of approximately 50% low nicotine/TSNA tobacco and 50% conventional tobacco; a step 3 tobacco product can be comprised of approximately 75% low nicotine/TSNA tobacco and 25% conventional tobacco; and a step 4 tobacco product can be comprised of approximately 100% low nicotine/TSNA tobacco and 0% conventional tobacco. A tobacco use cessation kit can comprise an amount of tobacco product from each of the aforementioned blends to satisfy a consumer for a single month program. That is, if the consumer is a one pack a day smoker, for example, a single month kit would provide 7 packs from each step, a total of 28 packs of cigarettes. Each tobacco use cessation kit would include a set of instructions that specifically guide the consumer through the step-by-step process. Of course, tobacco products having specific amounts of nicotine and/or TSNAs would be made available in conveniently sized amounts (e.g., boxes of cigars, packs of cigarettes, tins of snuff, and pouches or twists of chew) so that consumers could select the amount of nicotine and/or TSNA they individually desire. There are many ways to obtain various low nicotine/low TSNA tobacco blends using the teachings described herein and the following is intended merely to guide one of skill in the art to one possible approach.

To obtain a step 1 tobacco product, which is a 25% low nicotine/TSNA blend, prepared tobacco from an approximately 0 ppm nicotine/TSNA tobacco can be mixed with conventional Burley, Flue-cured, or Oriental in a 25%/75% ratio respectively to obtain a Burly tobacco product having 22,500 ppm nicotine and 6,000 ppb TSNA, a Flue-cured product having 15,000 ppm nicotine and 225 ppb TSNA, and an Oriental product having 7,500 ppm nicotine and 75 ppb TSNA. Similarly, to obtain a step 2 product, which is 50% low nicotine/TSNA blend, prepared tobacco from an approximately 0 ppm nicotine/TSNA tobacco can be mixed with conventional Burley, Flue-cured, or Oriental in a 50%/50% ratio respectively to obtain a Burly tobacco product having 15,000 ppm nicotine and 4,000 ppb TSNA, a Flue-cured product having 10,000 ppm nicotine and 150 ppb TSNA, and an Oriental product having 5000 ppm nicotine and 50 ppb TSNA. Further, a step 3 product, which is a 75%/25% low nicotine/TSNA blend, prepared tobacco from an approximately 0 ppm nicotine/TSNA tobacco can be mixed with conventional Burley, Flue-cured, or Oriental in a 75%/25% ratio respectively to obtain a Burly tobacco product having 7,500 ppm nicotine and 2,000 ppb TSNA, a Flue-cured product having 5,000 ppm nicotine and 75 ppb TSNA, and an Oriental product having 2,500 ppm nicotine and 25 ppb TSNA.

It should be appreciated that tobacco products are often a blend of many different types of tobaccos, which were grown in many different parts of the world under various growing conditions. As a result, the amount of nicotine and TSNAs will differ from crop to crop. Nevertheless, by using conventional techniques one can easily determine an average amount of nicotine and TSNA per crop used to create a desired blend. By adjusting the amount of each type of tobacco that makes up the blend one of skill can balance the amount of nicotine and/or TSNA with other considerations such as appearance, flavor, and smokability. In this manner, a variety of types of tobacco products having varying level of nicotine and/or nitrosamine, as well as, appearance, flavor and smokeability can be created.

The foregoing is illustrative of the present invention, and is not to be construed as limiting thereof. The invention is defined by the following claims, with equivalents of the claims to be included therein. All references cited herein are hereby expressly incorporated by reference.

What which is claimed is:

1. An isolated nucleic acid consisting of SEQ Id NO: 1.

* * * * *

UNITED STATES PATENT AND TRADEMARK OFFICE
CERTIFICATE OF CORRECTION

PATENT NO. : 6,911,541 B2
DATED : June 28, 2005
INVENTOR(S) : Conkling et al.

It is certified that error appears in the above-identified patent and that said Letters Patent is hereby corrected as shown below:

Column 23,
Line 45, should read -- 1. An isolated nucleic acid consisting of SEQ ID NO: 1. --.

Signed and Sealed this

Twenty-seventh Day of December, 2005

JON W. DUDAS
*Director of the United States Patent and Trademark Office*